United States Patent
Van Ooijen et al.

(10) Patent No.: US 12,148,535 B2
(45) Date of Patent: Nov. 19, 2024

(54) INCREMENTALLY OPTIMIZED PHARMACOKINETIC AND PHARMACODYNAMIC MODEL

(71) Applicant: KONINKLIJKE PHILIPS N.V., Eindhoven (NL)

(72) Inventors: Hendrik Jan Van Ooijen, Wijk en Aalburg (NL); Bart Jacob Bakker, Eindhoven (NL); Rene Van Den Ham, Maarsbergen (NL)

(73) Assignee: Koninklijke Philips N.V., Eindhoven (NL)

( * ) Notice: Subject to any disclaimer, the term of this patent is extended or adjusted under 35 U.S.C. 154(b) by 589 days.

(21) Appl. No.: 16/618,571

(22) PCT Filed: Jun. 28, 2018

(86) PCT No.: PCT/EP2018/067391
§ 371 (c)(1),
(2) Date: Dec. 2, 2019

(87) PCT Pub. No.: WO2019/002451
PCT Pub. Date: Jan. 3, 2019

(65) Prior Publication Data
US 2020/0161006 A1  May 21, 2020

(30) Foreign Application Priority Data
Jun. 28, 2017 (EP) .................................... 17178406

(51) Int. Cl.
*G16H 70/40* (2018.01)
*C12Q 1/56* (2006.01)
*G01N 33/86* (2006.01)
*G16B 40/00* (2019.01)
*G16C 20/30* (2019.01)
*G16H 20/10* (2018.01)
*G16H 50/50* (2018.01)
*G16C 20/70* (2019.01)

(52) U.S. Cl.
CPC .............. *G16H 70/40* (2018.01); *C12Q 1/56* (2013.01); *G01N 33/86* (2013.01); *G16B 40/00* (2019.02); *G16C 20/30* (2019.02); *G16H 20/10* (2018.01); *G16H 50/50* (2018.01); *G01N 2333/745* (2013.01); *G16C 20/70* (2019.02)

(58) Field of Classification Search
CPC ........ G16H 70/40; G16H 50/50; G16H 20/10; G16C 20/30; G16B 40/00; C12Q 1/56; G01N 33/86
See application file for complete search history.

(56) References Cited

U.S. PATENT DOCUMENTS

2010/0273738 A1   10/2010   Valcke et al.
2013/0179184 A1    7/2013   Hurst
2016/0300037 A1   10/2016   Mould

FOREIGN PATENT DOCUMENTS

EP   2538360 A1    12/2012
WO   2012079576 A1  6/2012
WO   2012172481 A1 12/2012

OTHER PUBLICATIONS

Delavenne et al: "Investigation of Pk-Pd Drug-Drug Interaction Between Acenocoumarol and Amoxicillin Plus Clavulanic Acid"; Fundamental & Clinical Pharmacology, vol. 23, 2009, pp. 127-135.
Nayak et al: "Using a Systems Pharmacology Model of the Blood Coagulation Network to Predict the Effedcts of Various Therapies on Biomarkers": CPT Pharmacometrics Systl Paharmacol. (2015), vol. 4, pp. 396-405.
Nielsen: "Modellin in Oral Anticoagulation Treatment"; Phd Thesis, Aalbortg University, Denmark, 2010, 33 Page Document.
PCT/EP2018/067391 ISR & WO, Aug. 21, 2018, 26 Page Document.
Sagar et al: "Dynamic Modeling of the Human Coagulation Cascade Using Reduced Order Effective Kinetic Models"; School of Chemical and Biomolecular Engineering, Cornell University, Published Mar. 2015, 26 Page Document.
Wajima et al: :A Comprehensive Model for the Humoral Coagulation Network in Humans; Nature: vol. 86, No. 3, Sep. 2009 pp. 290-298.
Zi et al: "In Silico Identification of the Key Components and Steps in IFN-y Induced JAK-STAT Signaling Pathway"; FEBS Letters 579 (2005) pp. 2201-1108.

*Primary Examiner* — Jerry Lin

(57) ABSTRACT

The invention relates to a method for predicting a value of a parameter of a system (20). The value of the parameter of the system (20) is predicted by incrementally optimizing a pharmacokinetic and pharmacodynamic model based on values of parameters of the system (20) received over time. This allows for predicting values of the parameters of the system (20) with improved accuracy. In one embodiment the system (20) comprises a coagulation system (21) comprising an anticoagulant. The predicted value of the parameter of the system (20) can be a point in time at which the coagulation system (21) reaches hemostatic balance after a periodic supply of anticoagulant to the coagulation system (21) is discontinued.

14 Claims, 12 Drawing Sheets

INCREMENTALLY OPTIMIZED PHARMACOKINETIC AND PHARMACODYNAMIC MODEL

CROSS-REFERENCE TO PRIOR APPLICATIONS

This application is the U.S. National Phase application under 35 U.S.C. § 371 of International Application No. PCT/EP2018/067391, filed on Jun. 28, 2018, which claims the benefit of European Patent application Ser. No. 17/178, 406.9, filed on Jun. 28, 2017. These applications are hereby incorporated by reference herein.

FIELD OF THE INVENTION

The present invention relates to a method for predicting a value of a parameter of a system, and in particular but not exclusively to interacting with a drug using a pharmacokinetic and pharmacodynamic model (PKPD model).

BACKGROUND OF THE INVENTION

The interaction between a system and a drug can be modeled using a PKPD model. A PKPD model combines a pharmacokinetic model (PK model) and a pharmacodynamic model (PD model). A PK model describes how a system affects a drug supplied to that system. A PD model describes how the drug affects the system. The system can for example be a patient or subject. The subject can comprise a coagulation system which can for example be a set of reactions occurring in the subject, e.g. a human subject, in response to a coagulation trigger, for example a vascular injury. A coagulation system comprises proteins, regulators, and inhibitors that interact in order to generate a coagulation cascade or coagulation process that allows transforming a liquid to a gel that eventually forms a clot. A PKPD model can for example be applied to a coagulation system that is periodically supplied with an anticoagulant in order to study the interaction between the coagulation system and the anticoagulant.

In particular subjects at high risk for thrombosis are periodically supplied with anticoagulants, typically vitamin K antagonists (VKA) to lower their thrombosis risk, i.e., the risk of formation of a blood clot in a blood vessel that blocks the blood flow. Thrombosis risk can for example occur due to internal factors, such as a malfunction in the coagulation process of the subject, e.g. a pathological condition that continuously or temporarily triggers the coagulation process, or external factors, such as being bedridden. Various anticoagulants can be used in order to affect the coagulation process. For example, the VKAs acenocoumarol and warfarin decrease the availability of a reduced form of vitamin K that is needed for the synthesis of coagulation factors II, VII, IX, and X and anticoagulant proteins C, S and Z in the liver of the subject. The coagulation factors II, VII, IX, and X are used in the coagulation process in order to form a blood clot. By inhibiting the production of these coagulation factors by VKAs the thrombosis tendency of subjects at risk is lowered. VKAs are given for long periods and typically subjects receive them throughout their life based on a medicinal schedule that determines dose, i.e. amount of VKA, and time intervals for supplying the subject with VKA.

If subjects with high thrombosis risk receiving VKA are scheduled for a surgery with moderate to high bleeding risk they need to discontinue their VKA treatment, i.e., the periodic supply of VKA, a certain period of time before the surgery is performed in order to avoid excessive blood loss during surgery. Anticoagulant treatment, i.e. periodic supply of anticoagulant is generally stopped according to standardized guidelines, which take into account the type of anticoagulant treatment (e.g. acenocoumarol, warfarin, phenprocoumon) and its half-life in the general population. As a result of these guidelines all subjects are taken off their anticoagulant medication a fixed number of days before their surgery is planned.

WO 2012/172481 A1 discloses a simultaneous graphical representation, a risk of bleeding and a risk of thrombosis providing a visualized bridge therapy process. Furthermore, it discloses a computer-based prediction of the haemostatic situation of the examined blood circulation by using a combination of a biochemical model and a pharmacokinetic model for calculation or another mathematical representation of the blood circulation.

SUMMARY OF THE INVENTION

It can be seen as an object of one embodiment of the invention to provide a method, computer program and decision support system which allow more accurate predictions of a value of a parameter of a system.

In a first aspect of the present invention, a computer-implemented method for predicting a value of a parameter of a coagulation system comprising an anticoagulant periodically supplied to the system is presented, wherein the value of the parameter of the system is predicted by incrementally optimizing a pharmacokinetic and pharmacodynamic model based on values of sensitive parameters of the system received over time; wherein the method comprises the steps of: receiving initial values of the parameters of the system, receiving a value or values of one or more of the parameters of the system, selecting one or more parameters of the system sensitive to the effects of the anticoagulant, and predicting the value of the parameter of the system based on current values of the one or more sensitive parameters of the system using the pharmacokinetic and pharmacodynamic model, wherein the one or more sensitive parameters of the system are used to optimize the pharmacokinetic and pharmacodynamic model, wherein the steps of receiving a value or values of one or more of the parameters of the system and predicting the value of the parameter of the system are repeated until occurrence of a predetermined event.

In one embodiment, since the PKPD model is incrementally optimized by receiving values of parameters of the system over time, the prediction of the value of the parameter of the system can be more accurate. The system can be in interaction with a drug, such as an anticoagulant. In this case there can be different responses for the different systems to the drug as the values of the parameters of the system can vary widely between two different systems. Even though it may in principle be possible to measure values for all parameters of each system, this induces high costs. In one embodiment, the present method allows predicting the value of a parameter of interest for reduced costs as a smaller number of values of parameters of the system need to be measured and to be received by the method in order to predict the value of the parameter of interest.

The method can predict one or more values of one or more parameters, i.e., the method can predict one value of one parameter, several values of one parameter, one value of several parameters, or several values of several parameters. Hence the method can be understood to predict at least one value of at least one parameter of the system.

The values of the parameters of the system can be time dependent, for example concentration values of proteins changing over time. The predicted value of the parameter of the system can for example be a time it takes for the system to reach a predetermined state, for example indicated by a parameter value reaching a predetermined threshold. The predicted value can also for example be a concentration value or in case of predicting several values of several parameters, concentration values of one or more proteins can be predicted.

The PKPD model can for example be based on a PK model and a PD model. The PKPD model can for example be based on the PK model of acenocoumarol as described by Delavenne et al in "Investigation of PK-PD drug-drug interaction between acenocoumarol and amoxicillin plus clavulanic acid", Fundam Clin Pharmacol. 2009; 23(1); 127-135, and the PD model of the VKA cycle and coagulation factor production described by Wajima et al in "A comprehensive Model for the Humoral Coagulation Network in Humans", Clin. Pharmacol Ther. 2009; 86(3); 290-298, which both are incorporated herein by reference.

In an embodiment the method comprises the steps of:
receiving initial values of the parameters of the system,
receiving a value or values of one or more of the parameters of the system, and
predicting the value of the parameter of the system based on current values of the parameters of the system using the PKPD model. The steps of receiving a value or values of one or more of the parameters of the system and predicting the value of the parameter of the system are repeated until occurrence of a predetermined event.

The initial values of the parameters of the system can for example be derived from literature, estimations, simulations or by measurements performed on the system, e.g., by taking a sample, such as a blood sample, from the system and performing measurements on the sample. The initial values of the parameters of the system can comprise one value for each parameter of the system. For one or more of the parameters more than one initial value can be received, for example a population distribution, i.e., several values for different individuals of which a value may be identical for some of the individuals.

The received value or values of one or more of the parameters of the system are derived from a measurement performed on the system, e.g. from a measurement performed on a blood sample, or by a simulation of the system that predicts the value or values.

The step of predicting the value of the parameter of the system based on current values of the parameters of the system using the PKPD model can comprise a step of generating a random sample of a number of samples based on the current values of the parameters. For example, 100, 500, 1000, or 5000 samples can be generated by random sampling, Latin hypercube sampling or any other sampling method that allows to generate a number of samples from a multidimensional model parameter distribution. In this case one of the values of each of the parameters that comprise more than one value, for example a population distribution, is essentially randomly selected for each of the samples and each sample has only one value for each parameter.

The step of predicting the value of the parameter of the system based on current values of the parameters of the system using the PKPD model can further comprise a step of calculating an average, median or other relevant value of each of the parameters of the system from values of the parameters calculated with the PKPD model from each of the samples generated from the random sampling. The current values of the parameters of the system can comprise a system characteristic of the system which can improve the prediction.

In an embodiment the system comprises a coagulation system comprising an anticoagulant. The anticoagulant can for example be periodically supplied to the coagulation system. The parameters of the system can comprise parameters of the coagulation system. Hence parameters that are parameters of the system can also be parameters of the coagulation system.

In another embodiment, the system can comprise a pain signaling system comprising an analgesic, a tumor system comprising an anti-tumor drug such as chemotherapy and/or targeted therapy, an inflammatory system comprising an anti-inflammatory drug, or a blood pressure system comprising a blood pressure modulating agent.

The value of the parameter predicted by the method can be a value of a parameter that allows to determine a time interval or a point in time at which the coagulation system comprising the anticoagulant reaches hemostatic balance, i.e. a state of normal coagulation, after discontinuing a periodic supply of anticoagulant to the coagulation system. The anticoagulant can for example be a VKA, such as acenocoumarol, warfarin, phenprocoumon, or any other VKA or anticoagulant known to the person skilled in the art. A coagulation system, e.g. of a subject, is in hemostatic balance if the coagulation system has a tendency for thrombosis or bleeding that is essentially the same as for an average coagulation system, e.g. the population average. Hence a coagulation system in which essentially all anticoagulant affected proteins are essentially recovered to their normal values, i.e., the values without anticoagulant treatment of the coagulation system, is considered to be in hemostatic balance.

In another embodiment, values of more than one parameter of the system can be predicted by the method. The values of the parameters can for example allow to determine whether the coagulation system is in a predetermined state or the point in time when the coagulation system will reach a predetermined state, such as hemostatic balance.

In another embodiment, values of one parameter of the system over time can be predicted by the method, e.g. values of a parameter sensitive to the effects of anticoagulant over time, such as international normalized ratio (INR) or thrombin generation assay (TGA) values over time. For example, a coagulation system with an INR value between 0.8 and 1.2 is generally considered to be in hemostatic balance, as normal INR values of the population average are between 0.8 and 1.2. In case that a coagulation system, e.g., of a subject, is in hemostatic balance, a surgical procedure can be performed with a normal bleeding risk. The predetermined state can also be a state in which a surgical procedure can be performed with an acceptable bleeding risk. A coagulation system is generally considered to be in a state with acceptable bleeding risk if sufficient coagulation occurs. Sufficient coagulation is generally considered to occur for a coagulation system with an INR value below 1.5.

Furthermore, the values of several parameters over time can be predicted by the method, for example concentration values of various proteins, such as coagulation factors II, VII, IX, X, and protein C, over time.

In another embodiment, the parameters of the system can comprise a system characteristic of the system. A system characteristic is here to be understood as at least one system characteristic, i.e. one or more system characteristics.

A system characteristic of the system can for example be system weight, system volume, one or more compartment volumes, drug doses, such as anticoagulant doses supplied to the system, time intervals of drug doses supplied to the system, and timing of drug doses supplied to the system. The system can comprise a body. In this case one of the parameters can be body weight. A system characteristic of the system can also for example be the half maximal inhibitory concentration IC50 for the anticoagulant.

In another embodiment, the received value or values of one or more of the parameters of the system comprise a value of a parameter of the coagulation system sensitive to the effects of the anticoagulant. The received values can also comprise several values of a parameter of the coagulation system sensitive to the effects of the anticoagulant. Hence the received value or values comprise at least one value of a parameter of the coagulation system sensitive to the effects of the anticoagulant.

A parameter of the coagulation system sensitive to the effects of the anticoagulant can for example be a concentration of a protein. The concentration values of the proteins can for example be determined based on a sample, such as a blood sample, derived from the system. The concentration values can be expressed in mol/l. Various tests or measurements known to the person skilled in the art, for example coagulation factor activity assays or coagulation factor antigen tests, can be performed on the blood sample in order to determine the concentration values of the proteins.

For example, if the anticoagulant is a VKA, parameters of the coagulation system sensitive to the effects of the anticoagulant can for example be the concentration of coagulation factors II, VII, IX, X, and protein C. Such parameter can furthermore be the concentration of protein S and/or protein Z.

A parameter of the coagulation system sensitive to the effects of the anticoagulant can furthermore for example be derived from functional measurements performed on the system such as prothrombin time (PT), INR, activated partial thromboplastin time (aPTT), TGA, or any other measurement indicating coagulation or anticoagulation.

In one embodiment, a sensitive parameter of the system is selected from the parameters of the system. The sensitive parameter of the system is used to optimize the PKPD model. In another embodiment, several sensitive parameters of the system can be selected from the parameters of the system and they can be used to optimize the PKPD model. Hence it is to be understood that one or more sensitive parameters can be selected. One or more sensitive parameters can also be selected from the parameters of the coagulation system. In particular sensitive parameters selected from the coagulation system can be used to optimize the PKPD model.

Sensitive parameters of the system are those parameters that have the highest impact on the prediction of the value of the parameter of the system predicted by the method and can for example be specific parameters of the PKPD model, i.e., model parameters, such as reaction rates or concentration values.

The sensitive parameter of the system can be selected by a sensitivity analysis. The sensitivity analysis can for example be a multi-parametric sensitivity analysis. The multi-parametric sensitivity analysis can for example be based on the drug, e.g. anticoagulant and/or the parameters of the system, i.e., based on the drug, based on the parameters of the system or based on the drug and the parameters of the system.

The multi-parametric sensitivity analysis can for example be performed as described by Zi et al. in "In silico identification of the key components and steps in IFN-gamma induced JAK-STAT signaling pathway", FEBS Lett., 2005; 579(5); 1101-108, incorporated herein by reference.

Additionally, the step of predicting the value of the parameter of the system based on current values of the parameters of the system using the PKPD model can comprise the step of:

optimizing a current value of the sensitive parameter of the system by minimizing a difference between the received value or values of one or more of the parameters of the system and its predicted current value or their predicted current values based on variation of the current value of the sensitive parameter of the coagulation system while keeping values of other parameters of the system fixed. Alternatively, current values of the sensitive parameters of the coagulation system can be optimized by minimizing a difference between the received value or values of one or more of the parameters of the system and its predicted current value or their predicted current values based on variation of the current values of the sensitive parameters of the coagulation system while keeping values of other parameters of the system fixed.

The minimization can for example be performed by a Markov Chain Monte Carlo (MCMC) optimization algorithm, the simplex algorithm, Newton's method, gradient descent, particle swarm optimization or any other mathematical model, method or algorithm that allows optimizing values of parameters. The MCMC optimization algorithm can for example minimize the sum of the log of the received values over the predicted current values by variation of the values of the sensitive parameters of the system while keeping other parameters of the system fixed. For example, if the system comprises a coagulation system, the received values can for example be concentration values of proteins that have been derived from measurements of the system, in particular the proteins can be coagulation factors II, VII, IX, X, and protein C. The received values can in another embodiment be values derived from functional measurements, such as values of INR or TGA.

In one embodiment one or more of the parameters have two or more initial values, for example a population distribution, and the step of receiving initial values of the parameters of the system comprises the step of:

generating a number of random samples from the initial values of the parameters as input for the prediction of the value of the parameter of the system.

For example, 100, 500, 1000, or 5000 samples can be generated by random sampling, Latin hypercube sampling or any other sampling method that allows to generate a number of samples from a multidimensional model parameter distribution. Each sample has one value for each of the parameters of the system. The samples can be used as input to the PKPD model, which can be used to calculate current values of the parameters for each of the samples. In order to optimize the calculation for example one or more of the parameters drug dose, such as anticoagulant dose supplied to the system, drug dosage timing and system weight can be parameters of the system. An average value for each of the parameters of the system can be calculated by summing over each of the values of each of the parameters of each of the samples and dividing by the number of samples.

In another embodiment, each of the samples of the number of samples can be used in the optimization process as input. The optimization process, for example the MCMC optimization algorithm, is performed iteratively generating a sample of values of the parameters of the system in each iteration step. The optimization process is performed for example as long as necessary to have convergence of the values of the sensitive parameters or until two consecutive values of the difference between the received value or values of one or more of the parameters of the system and its predicted current value or their predicted current values are below a predetermined threshold. The sample of each optimization process run with the lowest difference can be selected as a selected sample. The selected samples can be used as input to the PKPD model, which can be used to calculate current values of the parameters for each of the samples. In order to optimize the calculation one or more of the parameters in form of a system characteristic, e.g., drug dose supplied to the system, drug dosage timing, such as anticoagulant dosage timing and system weight can be parameters of the system. In another embodiment, IC50 can be a parameter in form of a system characteristic. The PKPD model therefore predicts values for each of the parameters for each of the selected samples. An average value of each of the parameters can be calculated by summing over each of the predicted values of each of the parameters of each of the selected samples and dividing by the number of selected samples. In subsequent prediction iteration steps of the method the selected samples can be used as input for the prediction. Alternatively, the initial sample or other randomly generated samples can be used as input for each subsequent prediction iteration step.

In one embodiment the predetermined event is that the method reaches a predetermined number of iteration steps. The predetermined event can also be that the coagulation system reaches hemostatic balance after discontinuing periodic supply of the anticoagulant to the coagulation system. The predetermined event can furthermore be that a difference between the predicted values of the parameter of the system between two subsequent iteration steps is below a predetermined threshold.

The value of the parameter of the system can for example be an INR value, a time until the INR value reaches a predetermined threshold value, a concentration value of a coagulation factor, or a time until one or more values of one or more coagulation factors reach predetermined threshold values. The values of the parameter of the system can for example be concentration values of a coagulation factor, such as a time progression of concentration values of the coagulation factor or INR values, such as a time progression of the INR value. The values of the parameters of the system can for example be concentration values of two or more coagulation factors, such as a time progression of concentration values of two or more coagulation factors or concentration values of one or more coagulation factors and INR values.

In one embodiment the method further comprises the step of:
performing an action (or indicating an action to be performed, e.g. via a user interface of a decision support system) based on the predicted value of the parameter of the system. The step of performing an action (or indicating an action to be performed) based on the predicted value of the parameter of the system is performed whenever the value of the parameter of the system is predicted. Alternatively, an action can be performed (or indicated to be performed) based on the predicted values of the parameter of the system or on the predicted values of the parameters of the system.

Actions performed (or indicated to be performed) based on the predicted value or values of the parameter or parameters of the system can for example be continuing supply of a drug to the system, for example anticoagulant to the coagulation system, discontinuing supply of a drug to the system, for example anticoagulant to the coagulation system, supplying of a drug to the system, for example vitamin K to the coagulation system, postponing a surgery, or skipping the step of performing an action.

In a further aspect of the present invention a decision support system and/or device is presented. The decision support system and/or device comprises:
a receiving unit for receiving values of parameters of a coagulation system comprising an anticoagulant, and
a system unit for predicting a value of a parameter of the system. The receiving unit is configured to supply received values of the parameters of the system to the system unit. The system unit is configured to select one or more parameters of the system sensitive to the effects of the anticoagulant and to predict the value of the parameter of the system by incrementally optimizing a PKPD model based on values of the one or more sensitive parameters of the system received over time, wherein the one or more sensitive parameters of the system are used to optimize the PKPD model.

The receiving unit can for example be connected to the system unit in order to provide the received values of the parameters of the system to the system unit. The receiving unit can also be included in a central unit of the decision support system that comprises the system unit and the receiving unit.

The system unit can be configured to predict one or more values of one or more parameters of the system by incrementally optimizing a PKPD model based on values of the parameters of the system received over time. The system unit can be any device that is able to perform calculations based on received data such as values of parameters in order to predict the value or values of the parameter or parameters of the system, for example a processor. The receiving unit can for example be connected to an external network, for example a hospital IT system that comprises data regarding systems, such as parameters of systems, or data regarding coagulations systems of the systems, for example, values of reaction rates, concentration values of proteins, system weights, body weights, drug doses supplied to the system, anticoagulant doses supplied to the coagulation system, time intervals of drug dosage, time intervals of anticoagulant dosage, point of time of drug dosage, point of time of anticoagulant dosage, or any other parameters of the system. The anticoagulant can be supplied to the system. If the anticoagulant is supplied to the system, it is also supplied to the coagulation system as part of the system. The external network, for example hospital IT system can furthermore comprise measurement results or test results, such as PT, aPTT, INR, TGA, or any other test that determine coagulation parameters.

The decision support system and/or device can have a visual display unit for displaying the value or values of the parameter or parameters predicted by the system unit. The visual display unit can for example be a display, screen, or monitor. The visual display unit can receive the value or values of the parameter or parameters from the system unit. The system unit and the visual display unit can be connected. The user can decide to perform an action based on the displayed value or values of the parameter or parameters predicted by the system unit. The system unit (e.g. visual display unit or other user interface thereof) can also indicate an action to be performed based on the predicted value of the parameter of the system. Hence the decision support system and/or device can support the user in taking a decision and to perform an action based on the information provided by the decision support system. Instead of a visual display unit the decision support system and/or device can for example comprise an audio unit for presenting the value or values of the parameter or parameters predicted by the system unit and/or indicated actions to be performed.

In one embodiment the decision support system and/or device comprises a user interface. The user interface is configured to supply received values of the parameters of the system to the system unit and to receive predicted values of the parameters of the system from the system unit. The user interface is furthermore configured to receive by a user using the decision support system as input to the decision support system a value of the parameter of the system and to provide to the user using the decision support system as output of the decision support system the value of the parameter predicted by the system unit. The user interface can also be configured to receive one or more values of one or more parameters of the system and to provide as output of the decision support system the value or values of the parameter or parameters predicted by the system unit. The user interface can also be configured to provide as output (e.g. on a display) an indication of an action to be performed.

The user interface can be connected to the receiving unit and/or the system unit. The user interface can for example comprise a touch display, graphical user interface, or any other interface that allows interaction with a user.

The decision support system and/or device can use any embodiments of the method of the present invention in order to determine the value or values of the parameter or parameters of the system. The decision support system and/or device allows to present content to the user that credibly assists the user in performing a technical task by means of a continued and guided human-machine interaction process.

The decision support system and/or device can comprise an additional drug unit that is configured for supplying a drug to the system. The additional drug unit can be controlled through the user interface by the user. The drug supply can also be automated in the sense that the drug supply is continued or discontinued by the additional drug unit in dependence of the predicted value of the parameter of the system.

In one embodiment of the decision support system and/or device, the decision support system and/or device comprises a computer readable medium. The computer readable medium can comprise data, such as values of parameters of the system, algorithms, and models, in particular the PKPD model.

In a further aspect of the present invention a computer program for predicting a value of a parameter of a coagulation system comprising an anticoagulant is presented. The computer program comprises program code means for causing a processor to carry out the method as defined in claim 1, when the computer program is run on the processor.

Other embodiments of the computer program can comprise program code means for causing a processor to carry out the method as defined in any of the dependent claims. The computer program can also be configured to be executed on the decision support system and/or device. The computer program can for example be stored on the computer readable medium of the decision support system in order to be executed on the decision support system. The computer program can alternatively or additionally be executed via an external network, i.e., the computer program can be a program that is executed on the external network, e.g. the internet, an intranet or a server, and that exchanges data with the decision support system and/or device.

In a further aspect of the present invention a computer readable medium is presented. The computer readable medium comprises the computer program according to claim 14.

Other embodiments of the computer readable medium can comprise embodiments of the computer programs that comprise program code means for causing a processor to carry out the method as defined in any of the dependent claims or any embodiment of the method. The computer readable medium can be configured to be used in a system connectable to the decision support system, e.g., the external network, or it can also be part of the decision support system or used in the decision support system, e.g., if the receiving unit is configured for receiving data from the computer readable medium.

It shall be understood that the method of claim 1, the decision support system of claim 12, the computer program of claim 14, and the computer readable medium of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

Embodiments of the invention are described by way of example with reference to the following drawings.

DETAILED DESCRIPTION OF EMBODIMENTS

Figure 1:
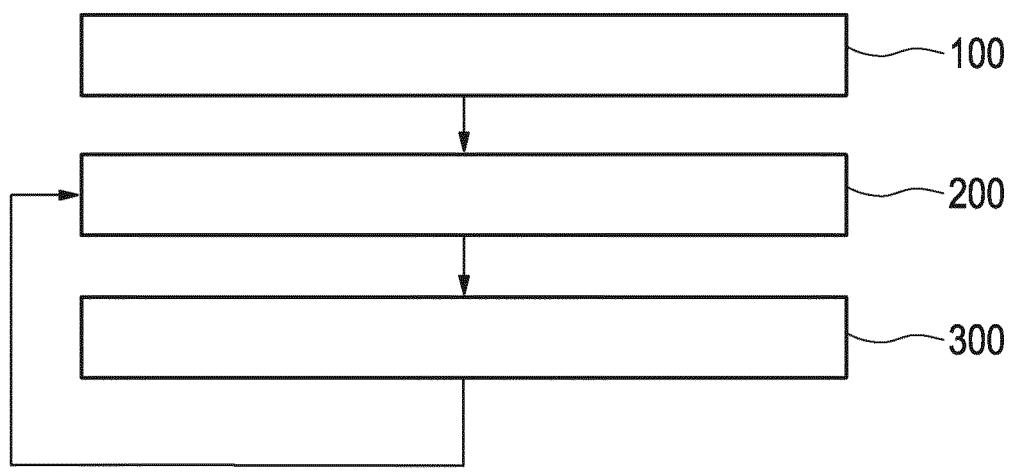
FIG. 1 shows a flow diagram of a first embodiment of the method.

FIG. 1 shows schematically and exemplarily a first embodiment of the method for predicting a value of a parameter of a system. In this embodiment the system comprises a coagulation system. In other embodiments the system can alternatively or additionally comprise any system that can be studied using a PKPD model, i.e., a system in interaction with a drug, such as a pain signaling system comprising an analgesic, a tumor system comprising an anti-tumor drug such as chemotherapy and/or targeted therapy, an inflammatory system comprising an anti-inflammatory drug, or a blood pressure system comprising a blood pressure modulating agent (not shown).

In this embodiment the value of the parameter of the system is also a value of a parameter of the coagulation system. The value of the parameter of the coagulation system is predicted by incrementally optimizing a PKPD model based on values of parameters of the system received over time. The PKPD model used in one embodiment is based on the PK model of acenocoumarol as described by Delavenne et al in "Investigation of PK-PD drug-drug interaction between acenocoumarol and amoxicillin plus clavulanic acid", Fundam Clin Pharmacol. 2009; 23(1); 127-135, and the PD model of the VKA cycle and coagulation factor production described by Wajima et al in "A comprehensive Model for the Humoral Coagulation Network in Humans", Clin. Pharmacol Ther. 2009; 86(3); 290-298. In other embodiments other PKPD models can be used (not shown). Hence the method is not limited to the specific PK model and PD model or combination of the PK and PD model to the PKPD model as presented for the embodiment of the method.

The method comprises the steps 100 to 300. In step 100 initial values of the parameters of the system are received. In step 200 an INR value of the coagulation system is received. In step 300 INR values of the coagulation system are predicted based on current values of the parameters of the coagulation system using the PKPD model. Steps 200 and 300 are repeated until the user decides to stop the method.

In other embodiments steps 200 and 300 can be repeated until the occurrence of a predetermined event. The predetermined event can be that the method reaches a predetermined number of iteration steps, that a difference between the predicted INR values of the coagulation system between two subsequent iteration steps is below a predetermined threshold or that the coagulation system reaches hemostatic balance after discontinuing periodic supply of an anticoagulant to the coagulation system.

The initial values of the parameters of the system in this embodiment comprise values for anticoagulant dose supplied to the system, anticoagulant timing and system weight. The anticoagulant dose supplied to the system is also supplied to the coagulation system, as the coagulation system is part of the system. The anticoagulant dose can for example be in a range between 0.5 and 7 mg/day, and in particular 3 mg/day of anticoagulant in case of acenocoumarol. The anticoagulant timing can for example be a 24 hour time interval. The system weight can for example be between 20 to 250 kg or up to 7000 kg. The aforementioned parameters are system characteristics and allow for optimizing the prediction of the PKPD model. Values of any other system characteristic can also be part of the initial values of the parameters of the system.

INR values of the coagulation system are received by performing a functional measurement in form of an INR measurement on a sample derived from the system. Each iteration of the method is performed at another point in time, i.e., the INR values of the coagulation system received are derived from functional measurements performed at different points in time. The first embodiment of the method predicts a time progression of INR values. A part of the INR values of the time progression can be received values derived from the system while other INR values of the time progression are predicted INR values. This allows predicting a point in time at which a coagulation system of a system in form of a subject reaches hemostatic balance and thus the subject can have surgery as sufficient coagulation by the subject's coagulation system is possible in order to avoid excessive blood loss. The coagulation system of the system can also be a simulation of a coagulation system of a subject or an artificial coagulation system, such as a system mimicking the functions of a coagulation system in form of a coagulation system of a subject, or a coagulation system of an artificial subject corresponding to an artificial coagulation system. For most surgeries an INR value of below 1.5 is regarded as sufficient for surgery, as the bleeding risk is acceptable while normal INR values in the population range from 0.8 to 1.2. A subject with high thrombosis risk that is treated with anticoagulants typically has an INR value of between 2.0 and 3.0 during anticoagulant treatment. The subject treated with anticoagulants can have a target INR value of up to 3.5 during anticoagulant treatment while INR values causing major bleeding risk can be as high as 8.0 to 10.0 and need immediate medical treatment, e.g., supplying the subject with vitamin K. Thus in order to have an acceptable INR value for subjects with high thrombosis risk, the supply with anticoagulants has to be discontinued a predetermined time before a surgery in order to allow for the INR value to reduce to a predetermined value. As the values of the parameters vary between the coagulation system of each system, e.g. subject, the reaction to anticoagulant treatment varies and the prediction which is true for one coagulation system cannot be transferred to another coagulation system. Hence it is useful in one embodiment to optimize the PKPD model for each individual coagulation system in order to increase the accuracy of the prediction.

In another embodiment in step 200 several values of parameters of the coagulation system sensitive to the effects of the anticoagulant can be received, for example concentration values of proteins, in particular of vitamin K affected proteins, such as coagulation factor II (FII), coagulation factor VII (FVII), coagulation factor IX (FIX), coagulation factor X (FX), and protein C (PC). Those values of parameters of the system can be received alternatively or additionally to the received INR value. The logarithm of the INR value is correlated with concentration values of the aforementioned parameters. The relation is given by $$INR = [FH]^{\beta_{FH}} \cdot [FVII]^{\beta_{FVII}} \cdot [FIX]^{\beta_{FIX}} \cdot [FX]^{\beta_{FX}} \cdot [PC]^{\beta_{PC}} \cdot 10^{\beta_0},$$

with $\beta_{FH} = -0.18$, $\beta_{FVII} = -0.29$, $\beta_{FIX} = 0.13$, $\beta_{FX} = -0.24$, $\beta_{PC} = -0.10$, $\beta_0 = -1.34$. The relation is based on the plots in the paper of Gulati et al., Arch. Pathol Lab Med 2011; 135; 490-494, which is incorporated herein by reference. The β parameters are fitted using 48 individuals from a study that are periodically supplied with VKA and 48 randomly sampled individuals that are not supplied with VKA.

In another embodiment, one or more values of one or more other parameters of the coagulation system sensitive to the effects of the anticoagulant, such as TGA can be received.

In another embodiment step 300 predicts values of several parameters, for example concentration values of proteins. In yet another embodiment step 300 predicts several values of another parameter, for example the time progression of the values of that parameter. In yet another embodiment step 300 predicts several values for several parameters, e.g., a time progression of the values of each of the parameters, for example the time progression of the concentration values of selected proteins. The values of the parameters predicted in step 300 are the current values for the next iteration step.

Figure 2:
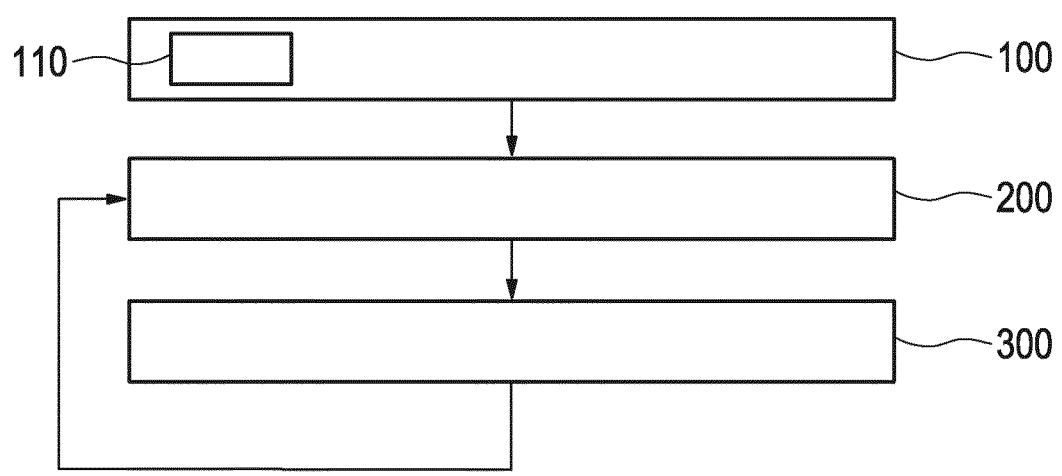
FIG. 2 shows a flow diagram of a second embodiment of the method.

FIG. 2 shows a flow diagram of a second embodiment of the method for predicting a value of a parameter of the system. The first embodiment of the method and the second embodiment of the method differ only in that the second embodiment comprises the additional step 110 of selecting sensitive parameters of the coagulation system. Step 110 is a substep of step 100.

The sensitive parameters are those parameters of the coagulation system that have the highest impact on the accuracy of the prediction of the PKPD model. In this embodiment the sensitive parameters are selected from the parameters of the coagulation system. The sensitive parameters can also be other parameters of the system, such as a compartment volume or clearance. The sensitive parameters are used to optimize the PKPD model.

In this embodiment the sensitive parameters are selected by a multi-parametric sensitivity analysis as described by Zi et al. in "In silico identification of the key components and steps in IFN-gamma induced JAK-STAT signaling pathway", FEBS Lett., 2005; 579(5); 1101-108. Other methods for selecting sensitive parameters by a sensitivity analysis, such as a local or multi-parametric sensitivity analysis can be used in other embodiments.

In another embodiment the sensitive parameters can also be selected based on expert judgment or from the literature. In another embodiment only one sensitive parameter of the coagulation system is selected.

Figure 3:
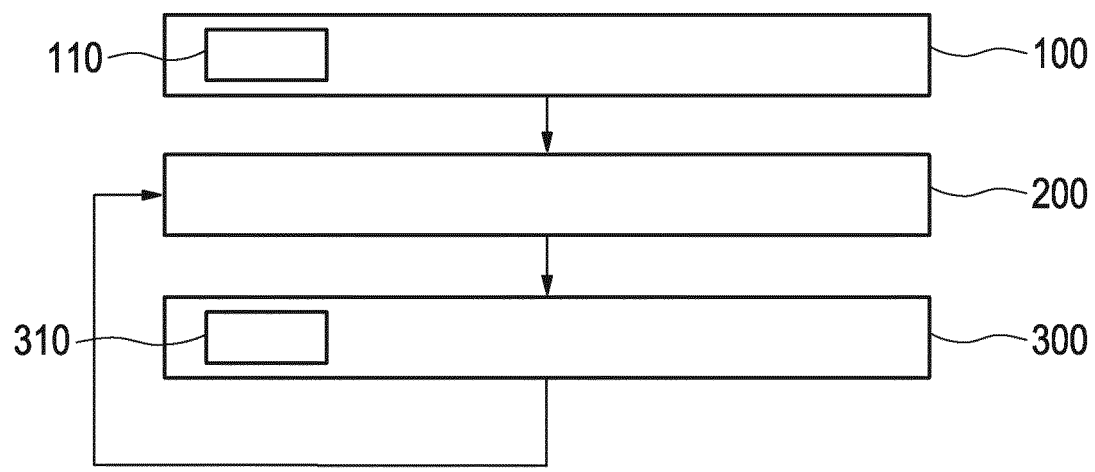
FIG. 3 shows a flow diagram of a third embodiment of the method.

FIG. 3 shows a flow diagram of a third embodiment of the method for predicting a value of a parameter of the system. The third embodiment of the method and the second embodiment of the method differ only in that the third embodiment comprises the additional step 310 of optimizing current values of the sensitive parameters of the coagulation system by minimizing a difference between the received INR value of the coagulation system and its predicted current value based on variation of the current values of the sensitive parameters of the coagulation system while keeping values of other parameters of the system fixed. Step 310 is a substep of step 300 and allows for an improved accuracy in the prediction of the value of one of the parameters, as the current values of the sensitive parameters are optimized and are then used as input to the PKPD model.

Alternatively, only one current value of only one sensitive parameter can be optimized. In this case only one sensitive parameter is varied while all other parameters are kept fixed in the optimization process. It is also possible to optimize the current value of only one sensitive parameter at a time and then optimize the current value of another sensitive parameter while keeping the values of previously optimized sensitive parameters and all other parameters fixed.

In this embodiment a MCMC optimization algorithm is used in order to optimize the current values of the sensitive parameters. In other embodiments other methods for optimizing values of parameters, such as the simplex algorithm, Newton's method, gradient descent or particle swarm optimization can be used.

In another embodiment step 310 optimizes current values of the sensitive parameters of the coagulation system by minimizing the sum of the log of the received concentration values over the predicted concentration values $$\left(E = \sum_i \log_{10}\left(\frac{received\_concentration\_value_i}{predicted\_concentration\_value_i}\right)\right)$$

by variation of the sensitive parameters while keeping the values of all other parameters of the system fixed. In yet another embodiment step 310 optimizes current values of the sensitive parameters of the coagulation system by minimizing the sum of the log of the received INR values over the predicted INR values $$\left(\sum_i \log_{10}\left(\frac{received\_INR\_value_i}{predicted\_INR\_value_i}\right)\right)$$

by variation of the sensitive parameters while keeping the values of all other parameters of the system fixed.

Figure 4:
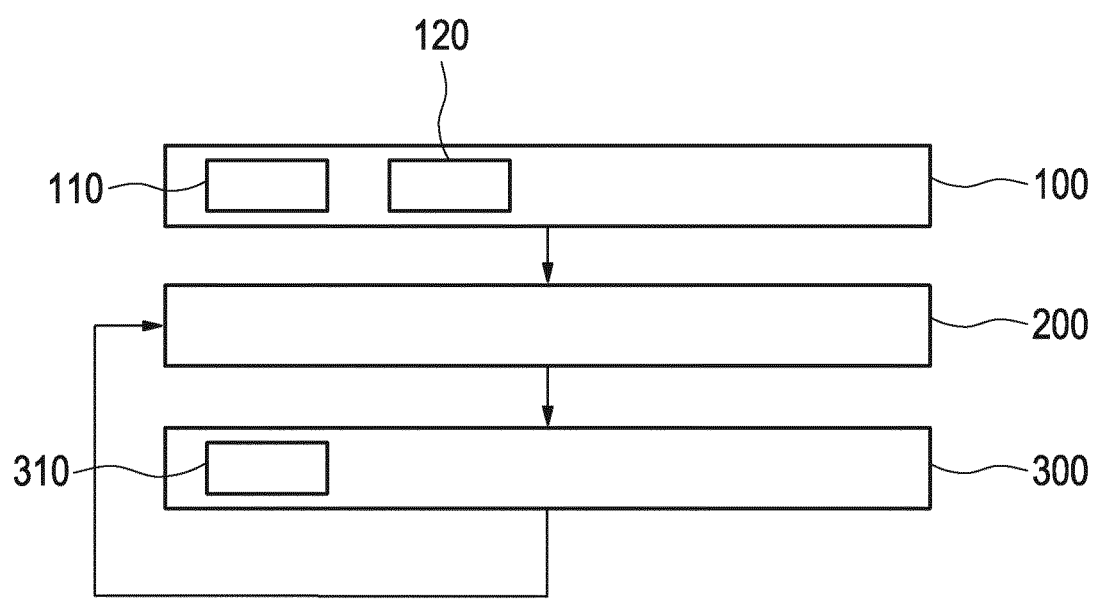
FIG. 4 shows a flow diagram of a fourth embodiment of the method.

FIG. 4 shows a flow diagram of a fourth embodiment of the method for predicting a value of a parameter of the system. The difference between the third embodiment of the method and the fourth embodiment of the method is that in the fourth embodiment of the method some of the parameters of the system have two or more initial values and the fourth embodiment of the method comprises an additional step 120 of generating a number of random samples from the initial values of the parameters as input for the prediction of the INR values. Step 120 is a substep of 100. In this embodiment the random samples are generated by Latin hypercube sampling based on the initial values of the parameters of the system, such that each sample has only one value for each parameter of the system that is sampled from the two or more initial values of the parameters of the system, e.g. from the population distribution. Any other sampling method, in particular random sampling method can also be used in order to generate the number of samples.

Step 120 allows for an increased accuracy of the method for predicting the value of the parameter, as a number of random samples can be used as input for the PKPD model to determine a number of values for each parameter which can be used to determine an average value. In particular, using the random samples, for example 100 random samples, each in a calculation using the PKPD model leads to 100 predicted INR value time progressions. From these 100 INR value time progressions an average INR value time progression can be determined.

Alternatively, an increased number of optimization calculations can be performed based on the random samples. In particular, each of the random samples can be used as input for the optimization process of step 310. Using again for example 100 random samples as input for the optimization process, the optimization leads to 100 optimized samples. In these samples the values of the sensitive parameters are optimized. However, as the values of the other parameters that are kept fixed during the optimization are sampled, they can vary between the different samples. The 100 optimized samples can then be used as input to the PKPD model in order to predict the INR value time progression with an improved accuracy. The optimized samples of each iteration of the step 310 can be used in subsequent steps as input for the optimization process which allows incrementally optimizing the PKPD model.

Alternatively, the initial samples can be used as input for the optimization process. In this case the received values of the parameters of each of the iterations of the step 200 are considered as additional values in order to incrementally optimize the PKPD model.

Instead of 100 random samples any reasonable number of random samples can be used, for example 200, 500, 1000, or 5000 random samples.

As for example the MCMC optimization algorithm generates a sample with values of each parameter in each iteration step of the MCMC optimization run, it is possible to select any one of the samples from the MCMC optimization run instead of the sample generated by the last step of the MCMC optimization run. In order to further improve the accuracy of the prediction of the INR value time progression the best sample with the lowest value of the aforementioned sum of log of the received INR value of the coagulation system over its predicted current value can be selected as optimized sample for each of the MCMC optimization runs. Other criteria for selecting the optimized sample can also be applied, e.g., the sample with the smallest error function, i.e., minimum of the sum of the log of the received concentration values over the predicted concentration values, or the sample with minimum of the sum of the log of the received concentration values over the predicted concentration values and smallest deviation from the population average.

Figure 5:
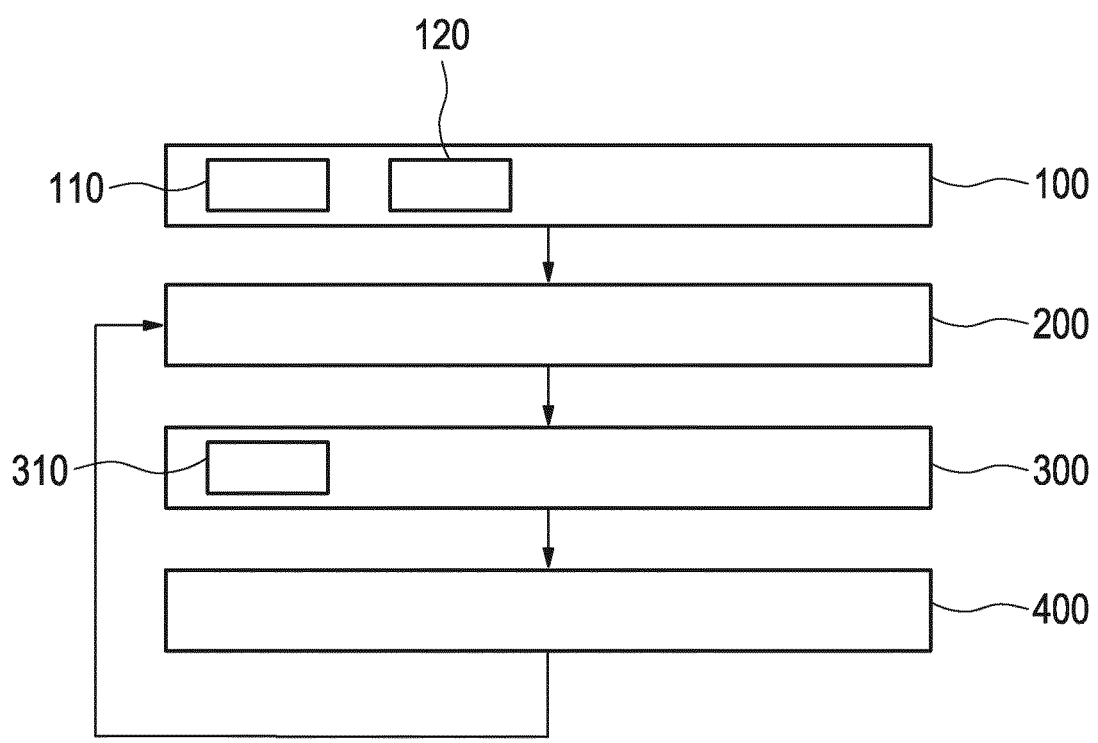
FIG. 5 shows a flow diagram of a fifth embodiment of the method.

FIG. 5 shows a flow diagram of a fifth embodiment of the method for predicting a value of a parameter of the system. The difference between the fifth embodiment of the method and the fourth embodiment of the method is that the fifth embodiment of the method comprises an additional step 400 of performing an action based on the predicted INR values of the coagulation system. Step 400 is performed whenever INR values of the system are predicted, i.e., after step 300 is performed.

Possible actions that can be performed are continuing supply of a drug to the system, for example anticoagulant to the coagulation system, discontinuing supply of a drug to the system, for example anticoagulant to the coagulation system, suppling a drug to the system, for example vitamin K to the coagulation system, or skipping the step of performing an action. Other actions can be to postpone or move forward a planned surgery.

In another embodiment the INR values in form of an INR value time progression can be displayed to a user using the method. Then the user using the method can decide which action is to be performed. The predicted INR value time progression can for example be displayed on a decision support system in order to credibly guide the user decision based on the internal state of the coagulation system.

In other embodiments the action can be performed based on other predicted values of the parameters of the system.

Figure 6:
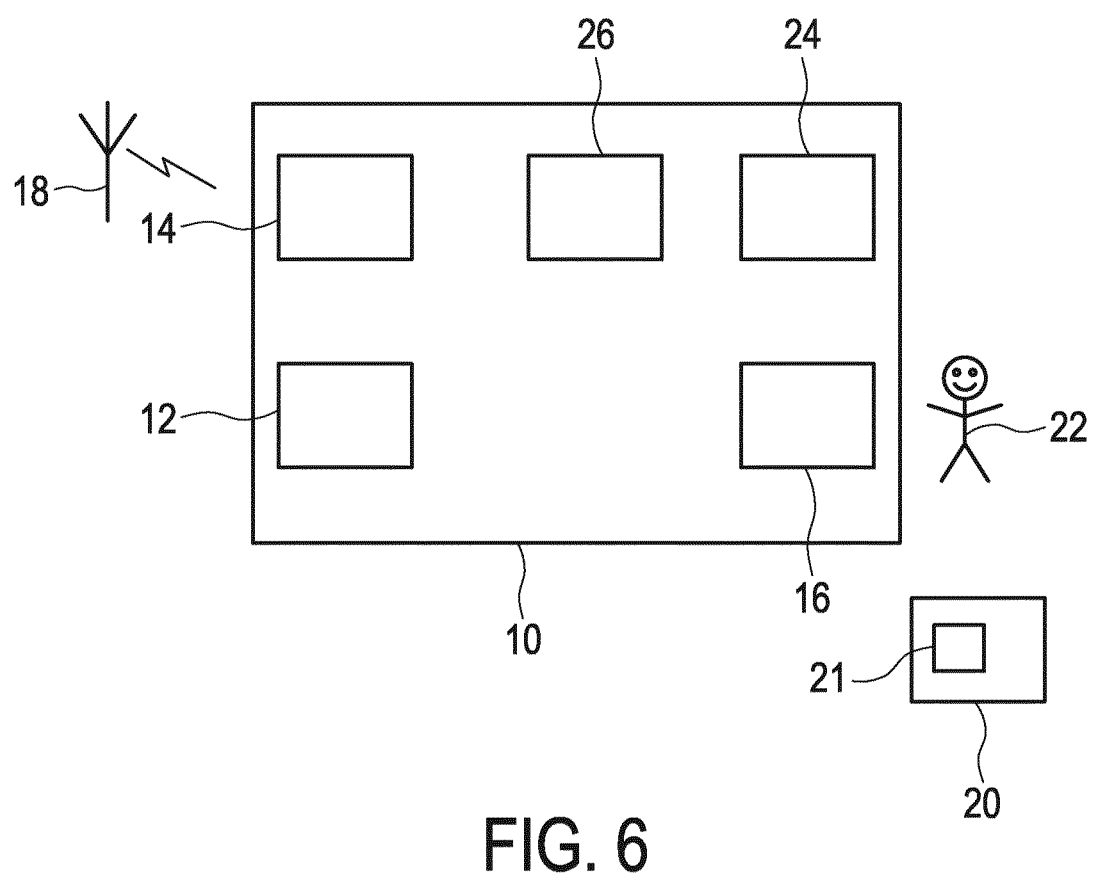
FIG. 6 shows an embodiment of a decision support system and/or device.

FIG. 6 shows an embodiment of a decision support system 10. The decision support system comprises a receiving unit 12 and a system unit 14. It will be appreciating the decision support system 10 can also be a device.

The receiving unit 12 receives values of parameters of a system 20. In this embodiment the system 20 comprises a coagulation system 21. The receiving unit 12 can furthermore receive values of parameters of the coagulation system 21. Values of parameters received from the coagulation system 21 are also values of parameters of the system 20, while values of parameters of the system 20 can be values of parameters of the coagulation system 21, but can also for example be values of another subsystem of the system 20 (not shown). System 20 can comprise other systems in which molecules of the system interact with drugs, such as a pain signaling system comprising an analgesic (not shown). The receiving unit 12 is connected to the system unit 14 in this embodiment. In other embodiments receiving unit 12 and system unit 14 can also be combined in a central unit (not shown). The receiving unit 12 supplies the values of the parameters received from the system 20 to the system unit 14.

The system unit 14 predicts values of parameters of the system 20. In order to predict the values of the parameters of the system 20 the system unit 14 incrementally optimizes a PKPD model based on values of the parameters of the system 20 received over time. In particular, the system unit 14 can perform each of the embodiments of the method as described for FIGS. 1 to 5.

In this embodiment the decision support system 10 further comprises a user interface 16. The user interface 16 is a graphical user interface in this embodiment that allows a user 22 to interact with the decision support system 10. Therefore, the user interface 16 has a display and buttons. In other embodiments user interface 16 can also be any other kind of user interface 16 that allows an interaction with a user 22, for example an audio interface that allows to enter information through voice or a touch display that allows to enter information by physical interaction with the touch display. In another embodiment the user interface 16 is replaced by a visual display unit, such as a monitor, display, or screen. The visual display unit can provide the user 22 with information from the decision support system 10, in particular with values of the parameters of the system 20 predicted by the system unit 14. In yet another embodiment the visual display unit can be replaced by an audio unit which provides the user 22 with information from the decision support system 10.

The user interface 16 is connected to the receiving unit 12 and the system unit 14. The user interface 16 receives values of the parameters of the system 20 by the user 22 using the decision support system 10 as input to the decision support system 10. The user interface 16 provides the received values of the parameters to the system unit 14. The system unit 14 predicts values of the parameters of the system 20 based on the received values. The system unit 14 supplies the predicted value of the parameters of the system 20 to the user interface 16. The user interface 16 provides to the user 22 the values predicted from the system unit 14 as output. The values predicted by the system unit 14 are therefore displayed to the user 22 which can perform an action based on the predicted values.

In another embodiment the decision support system 10 there is no user interface 16 present (not shown). Hence a user interface 16 is only optional. The interaction with the decision support system 10 can in this case for example be enabled by an external device connected to the decision support system 10 (not shown).

In this embodiment the receiving unit 14 is wirelessly connected to an external network 18. The external network 18 in this embodiment is a hospital IT system. The hospital IT system comprises data regarding coagulation systems 21 of systems 20, such as coagulation systems of subjects. Hence various values of parameters of the coagulation system 21 and the system 20 can be supplied to the decision support system 10 via the external network 18.

In this embodiment the decision support system 10 includes a computer readable medium 24 that comprises a computer program that comprises program code means that enable the system unit 14 to perform the embodiments of the methods described for FIGS. 1 to 5. The computer readable medium 24 is optional. Program code means can for example also be received via the external network 18 or they can also be stored on internal memory of the decision support system 10 (not shown).

In this embodiment the decision support system 10 includes an additional drug unit 26. The additional drug unit 26 can be controlled via the user interface 16. The additional drug unit 26 allows supplying a drug to the system 20. The additional drug unit 26 can also be controlled by the system unit 14. The additional drug unit 26 can supply a drug or discontinue supply of a drug, e.g., an anticoagulant or vitamin K, as an action performed based on the predicted values. The additional drug unit 26 is optional. Drug supply can for example also be manually controlled or performed. The additional drug unit 26 can for example also be programmed to periodically supply an anticoagulant until the system unit 14 or the user interface 16 issue a discontinue command.

The decision support system 10 or parts of the decision support system 10 can be arranged in the proximity of the system 20, and/or to the user 22 while other parts can be arranged with a distance to the system 20 and/or the user 22, e.g., in another room, building, or city. Parts of the decision support system 10 can for example be arranged in the internet, such as in the cloud or as a cloud service. Parts of the decision support system 10 can also be arranged on the external network, e.g., a hospital IT system.

The decision support system 10 can be used to perform each of the embodiments of the method according to FIGS. 1 to 5.

Figure 7:
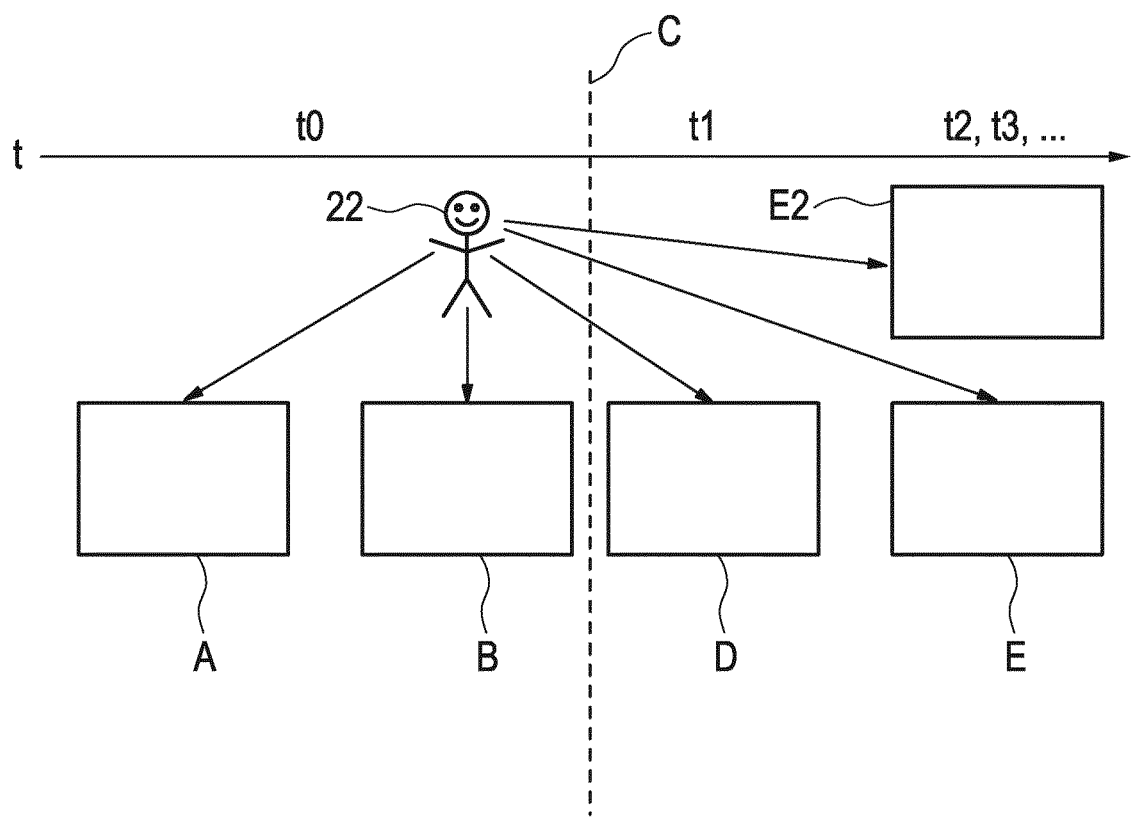
FIG. 7 shows schematically a setup for a clinical study.

FIG. 7 shows schematically a setup for a clinical study using five different methods, method A, method B, method D, method E, and method E2 for predicting FII, FVII, FIX, FX, and protein C of a coagulation system of a subject. Methods A, B, D, E, and E2 will be explained in the following. Method D, E and E2 correspond to embodiments of the present invention. The studied system is a coagulation system in form of a coagulation system of a human subject, but can also be an artificial human coagulation system or any other coagulation system or a simulation of such a coagulation system.

FIGS. 7 to 12 regard a clinical study that was performed including 12 subjects during a discontinuation of a specific anticoagulant, namely acenocoumarol and in some subject's re-initiation of acenocoumarol according to the standard guidelines of the MUMC hospital in Maastricht, The Netherlands. According to the performed clinical study subjects are required to stop acenocoumarol intake 4 days before a planned surgery. The discontinuation of anticoagulant supply denoted as the point in time C is performed between t0 and t1 (see FIG. 7). Blood samples are taken from each subject every day up to 5 days after the surgery (9 days in total). Blood samples are therefore taken at t1, t2, t3, and the following points in time, but not at t0. Taking a blood sample allows to derive values of parameters of the subject and therefore of the subject's coagulation system. From the blood samples the values of parameters of the system are derived through clinical measurements such as measurement of the concentration values of the vitamin K affected proteins, i.e., FII, FVII, FIX, FX, and PC. Furthermore, INR values are determined in these blood samples. For one subject, measurements of one day are not available, thus in total 107 measurement points are available. In addition, parameters in the form of system characteristics such as the dose of acenocoumarol and the timing of dosage are collected for all subjects throughout the study as well as the dose and time of the last acenocoumarol intake.

For all methods of the clinical study a PKPD model of a specific VKA, namely acenocoumarol is used based on a PK model of accenocoumarol described by Delavenne et al in "Investigation of PK-PD drug-drug interaction between acenocoumarol and amoxicillin plus clavulanic acid", Fundam Clin Pharmacol. 2009; 23 (1); 127-135, and a PD model of the VKA cycle and coagulation factor production described by Wajima et al in "A Comprehensive Model for the Humoral Coagulation Network in Humans", Clin Pharmacol Ther. 2009; 86 (3); 290-298. The PKPD model is implemented using MATLAB R2014a using an ordinary differential equation solver (ODE-solver). In particular, the ODE-solver ode23tb is used. Parameters of the PD model, such as reaction rates, etc. are tailored towards acenocoumarol. Other parameters and their population distribution are taken from the original papers. For example, normal concentration values in the population average are 1400 nM for FII, 10 nM for FVII, 90 nM for FIX, 170 nM for FX, and 65 nM for PC, with nM being nanomolar corresponding to $10^{-9}$ mol/L. The concentration values are distributed among different individuals, such that for example an individual can have a normal concentration value of 150 nM for FIX while the population average of 90 nM is much lower and at the same time the individual can have a concentration value of FX which is higher than for the population average.

Method A uses a personalized PKPD model based on the intake of acenocoumarol, i.e., taking into account the dose and time of acenocoumarol supply, and the body weight of each subject, which influences the value of other parameters of the system, namely the volume of the central compartment Vc and hence the distribution of the acenocoumarol. In method A system characteristics are considered for improving the PKPD model.

Initial values of the parameters of the system are provided by a user 22 of the method A. The initial values of the parameters of the system can also be provided by an external network, a database, or any other suitable way of providing information.

In method A the PKPD model is used to predict concentrations values of FII, FVII, FIX, FX, and PC for each subject using the subject's acenocoumarol dose and time, initial values in form of average population estimates of the parameters of the system as known to the skilled person from the literature including concentrations values of proteins and the subject's estimated Vc calculated using a default Vc corrected for the subject's body weight. The predicted concentration values of FII, FVII, FIX, FX and PC using method A are plotted on the vertical axis against the concentration values received from the clinical measurements performed on the blood samples on the horizontal axis for all days in FIG. 8A and for days 3 till 9 during the study in FIG. 9A. The concentration values are normalized to the normal concentration values of the population average.

Method B considers a so called inter-individual variability also referred to as population distribution reported in the publications of Delavenne et al. and Wajima et al. The inter-individual variability accounts for the uncertainty of the values of the parameters of various subjects and of the subject's coagulation systems. Each parameter of the system for which the value varies between different subjects therefore has various initial values in form of a population distribution taken from the literature.

The initial values of the parameters of the system are provided by the user 22 of the method B. The initial values of the parameters of the system can also be provided by an external network, a database, or any other suitable way of providing information.

In method B Latin hypercube sampling is used to generate 100 plausible samples from the multidimensional model parameter distribution. In another embodiment another number of plausible samples can be generated, for example 200, 500, 1000, or 5000 samples. The sampling process can lead to unplausible samples, i.e., physically impossible samples such as samples comprising negative values. In this case unplausible samples are excluded. Alternatively, sampling can be performed in the log-domain. In this case no negative values occur. Each sample has only one value for each parameter. For each subject the same PKPD model that was used for method A was used with each of the 100 plausible samples as input in order to predict 100 sets of values for each parameter. The method was furthermore personalized by taking into account the acenocoumarol dose and time and body weight. An average predicted concentration value for each of the parameters is determined by summing over all predicted concentration values of each parameter of each sample and dividing by the number of samples, i.e., by 100. The average predicted concentration values of FII, FVII, FIX, FX and PC using method B are plotted on the vertical axis against the concentration values received from the clinical measurements performed on the blood samples on the horizontal axis for all days in FIG. 8B and for days 3 till 9 during the study in FIG. 9B. The concentration values are normalized to the normal concentration values of the population average.

Method D is an embodiment of the invention and further improves the accuracy of the prediction of the values of the parameters of the system compared to the methods A and B.

The accuracy of the prediction of the concentration values of FII, FVII, FIX, FX and PC is improved by determining and selecting the most sensitive parameters of the PKPD model. The sensitive parameters are selected based on a regional multi-parametric sensitivity analysis using the population distributions of the values of the parameters of the system. The method as described by Zi et al. in "In silico identification of the key components and steps in IFN-gamma induced JAK-STAT signaling pathway", FEBS Lett., 2005; 579 (5); 1101-1108 is used in order to determine and select the most sensitive parameters. Any other method that allows determining the most sensitive parameters can also be used. For parameters for which no inter-individual variation, i.e. variation of values of the parameters between different systems and/or coagulation systems, is known according to the literature, a log-normal distribution of the values of the parameters with a standard deviation of 25% was assumed. In this case 5000 samples are drawn from the multidimensional model parameter distribution using Latin hypercube sampling. In addition, 5 dummy parameters that do not take part in the PKPD model are included in the sampling procedure to quantify the sampling effect, i.e. to determine a noise level of the sampling. Sensitivity coefficients of all parameters of the system, i.e. reaction rates, non-zero initial concentrations, and dummy parameters can be calculated using the method described by Zi et al using a sum of squared errors of the predicted concentration values of FII, FVII, FIX, FX, and PC and the received concentration values of FII, FVII, FIX, FX and PC on the first and all 9 days.

The following table comprises sensitive parameters with parameter names referring back to the model descriptions by Delavenne et al. and Wajima et al. selected from the list of parameters of the system having a sensitivity score significantly higher than that of the 5 dummy parameters in at least one of the calculated sum of squared errors based on first day only or all 9 days and based on expert judgment of the parameters of the system and their sensitivity results by the inventors.

| CL | IC50dVK2 | aPC |
| dVK | dX | [FII]0 |
| dVK2 | aII | [FVII]0 |
| dVKH2 | aVII | [FIX]0 |
| pVK | aIX | [FX]0 |
| IC50dVKO | aX | [PC]0 |

The parameters in the aforementioned table are the sensitive parameters of the PKPD model. For example the parameter dVK describes the degradation of vitamin K in the central compartment in form of the first-order degradation rate constant, dVK2 describes the first-order rate constant for the reduction from vitamin K to vitamin K hydroquinone (VKH2), dVKH2 describes the first-order rate constant for the oxidation from VKH2 to vitamin K epoxide (VKO), pVK describes the zero-order natural input rate of vitamin K from diet and other sources, dX describes the degradation of FX, i.e. the rate of FX decay, aX describes the rate of FX production by VKH2, and [x]0 describes the concentration of x, e.g., [FII]0 describes the concentration of FII.

Furthermore, method D uses received values derived from clinical measurements performed on the blood samples that are derived from each subject on the first day after discontinuation of supply with anticoagulant, i.e., at t1. The received values are the concentration values of FII, FVII, FIX, FX and PC.

Current values of the parameters are optimized by using a minimization algorithm based on a MCMC optimization algorithm. The MCMC optimization algorithm is allowed to tailor the values of the sensitive parameters to the received concentration values of FII, FVII, FIX, FX, and PC by minimizing the sum of the log of the received concentration value over the predicted concentration values $$\left( \sum_i \log_{10}\left( \frac{received\_concentration\_value_i}{predicted\_concentration\_value_i} \right) \right)$$

while keeping the values of all other parameters of the system fixed. The same method for generating 100 plausible samples as in method B is used in order to generate 100 plausible samples from the multidimensional model parameter distribution. The 100 plausible samples are used to start 100 MCMC chains. The chains are run long enough to get a stable sampling of the sensitive parameter distribution. In this embodiment the chains are run up to 5000 samples, although a stabilization of the error function, i.e. the error determined from the sum of the log of the received concentration values over the predicted concentration values, typically occurs after approximately 100 samples already. The MCMC chain can also be performed for any other number of steps, for example 200, 500, or 1000 steps generating 200, 500 or 1000 samples. The best sample from each MCMC chain based on the error function is selected. These selected optimized samples comprise current values of the sensitive parameters that are optimized and fixed values of the non-optimized parameters of the system. However, as random samples are used as inputs for the MCMC optimization algorithm the values of the non-optimized parameters can also have different values between different samples as they are sampled from the population distribution. The selection of the optimized samples leads to 100 optimized parameter sets. These 100 parameter sets are used to perform 100 simulations for each subject taking into account their respective doses and timings of acenocoumarol intake using the PKPD model. An average predicted concentration value for each of the parameters is determined by summing over all predicted concentration values of each parameter of each sample and dividing by the number of samples, i.e., by 100. The average predicted concentration values of FII, FVII, FIX, FX and PC predicted by method D are plotted on the vertical axis against the received concentration values of FII, FVII, FIX, FX and PC on the horizontal axis for all days in FIG. 8C and for days 3 till 9 during the study in FIG. 9C. The concentration values are normalized to the normal concentration values of the population average.

Method E is another embodiment of the present invention. Method E comprises essentially the same steps as Method D. However, received values of FII, FVII, FIX, FX and PC derived from both measurements at t2 and t1 are used for the optimization process instead of the received values at t1. After stabilization of the MCMC chains the optimized sample from each chain is selected based on the error function. The 100 optimized samples from this MCMC optimization are used as input to the PKPD model in order to predict concentration values of FII, FVII, FIX, FX and PC. An average predicted concentration value for each of the parameters is determined by summing over all predicted concentration values of each parameter of each sample and dividing by the number of samples, i.e., by 100. The average predicted concentration values of FII, FVII, FIX, FX and PC predicted by method E are plotted on the vertical axis against the received concentration values of FII, FVII, FIX, FX and PC on the horizontal axis for all days in FIG. 8D and for days 3 till 9 during the study in FIG. 9D. The concentration values are normalized to the normal concentration values of the population average.

In an alternative embodiment of method E, i.e. method E2, the best samples generated in method D are used as input for the MCMC optimization algorithm in order to optimize the current values of the sensitive parameters, instead of using the samples generated as described for method B.

Alternatively, or additionally to the received concentration values derived by measurements from the blood samples, functional measurements such as the INR or TGA can be performed on the blood samples in order to receive INR values or TGA values.

It can be derived from the setup presented in FIG. 7, and from FIG. 8 and FIG. 9 that the accuracy of the predicted concentration values increases by incrementally optimizing the PKPD model based on values of parameters of the system received over time. The accuracy can be further improved by using the optimized samples of method E2 for another optimization run in method E2 in which these optimized samples are used instead of the optimized samples derived from method D and received values of t3, t2, and t1 are considered. This allows an iterative optimization with each additional set of received values, i.e., received values of t4, t5, et cetera.

FIG. 10A to FIG. 10E show correlation graphs of predicted concentration values of FII, FVII, FIX, FX, and PC on the vertical axis compared to received concentration values of FII, FVII, FIX, FX, and PC on the horizontal axis. The concentration values are normalized to the normal concentration values of the population average. The predicted concentration values are predicted with method E based on received concentration values of FII, FVII, FIX, FX, and PC at the times t1, t2, and t3. The predicted concentration values show good agreement compared to the received concentration values.

Figure 8A:
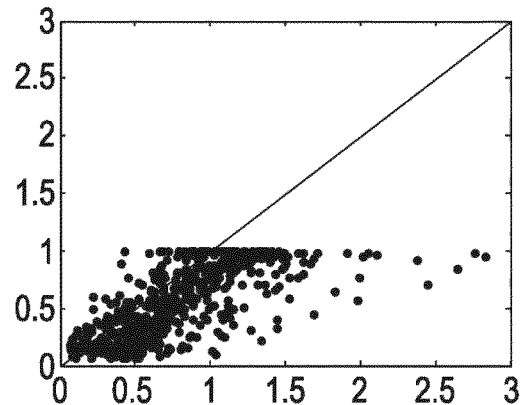
FIGS. 8A to 8D show four correlation graphs of four different methods for predicted concentration values compared to received concentration values of 5 coagulation factors for the study setup of FIG. 7 for values received over 9 days.
Figure 8B:
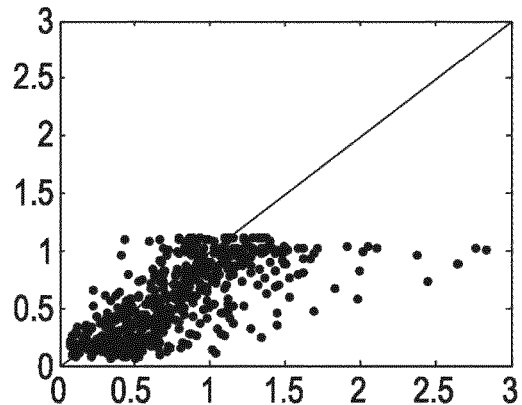
Figure 8C:
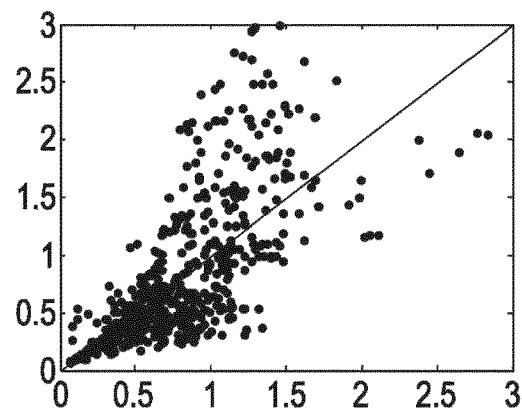
Figure 8D:
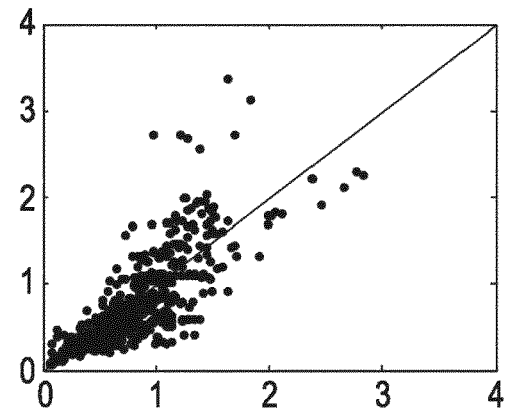
Figure 9A:
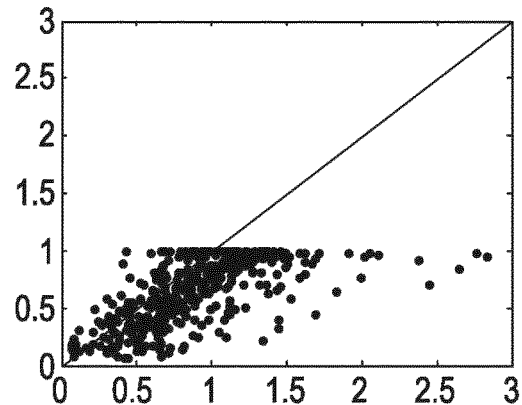
FIG. 9A to 9D show four correlation graphs of four different methods for predicted concentration values compared to received concentration values of 5 coagulation factors for the study setup of FIG. 7 for values received over 6 days.
Figure 9B:
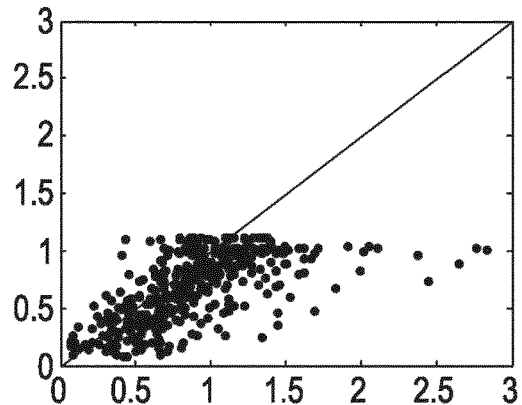
Figure 9C:
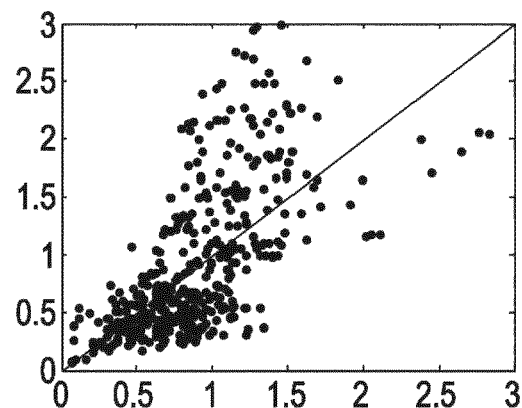
Figure 9D:
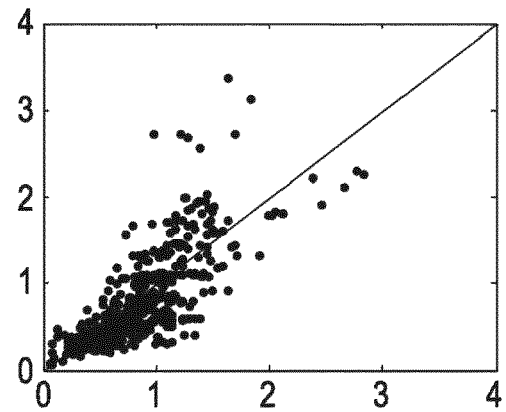
Figure 10A:
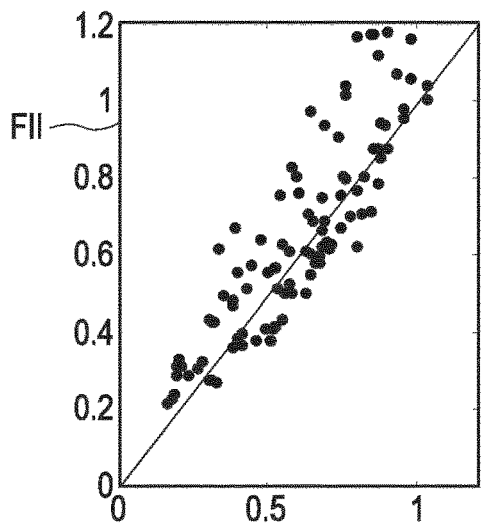
FIG. 10A to 10E show five correlation graphs of predicted values compared to received values of 5 coagulation factors for the study setup of FIG. 7 predicted by an embodiment of the method based on received values of the 5 coagulation factors.
Figure 10B:
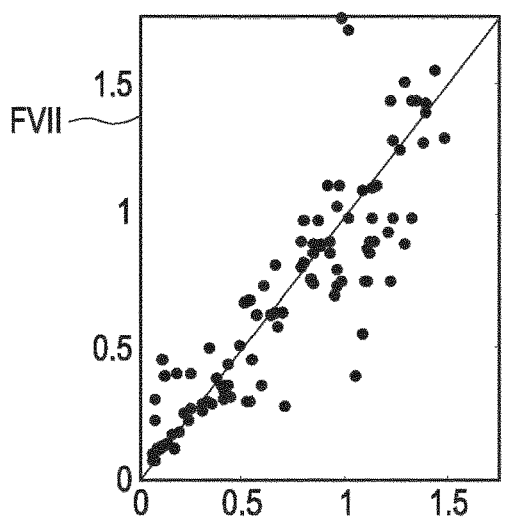
Figure 10C:
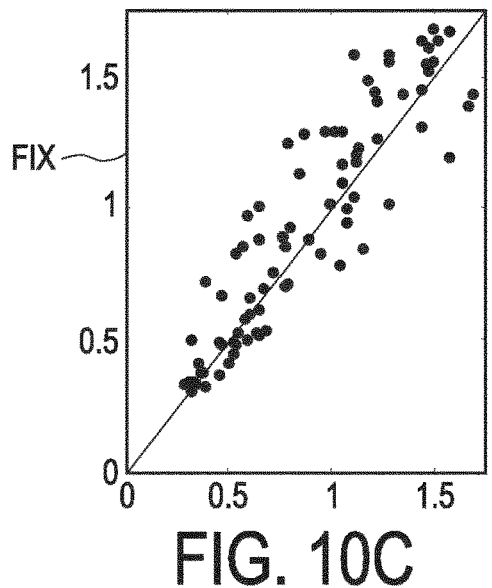
Figure 10D:
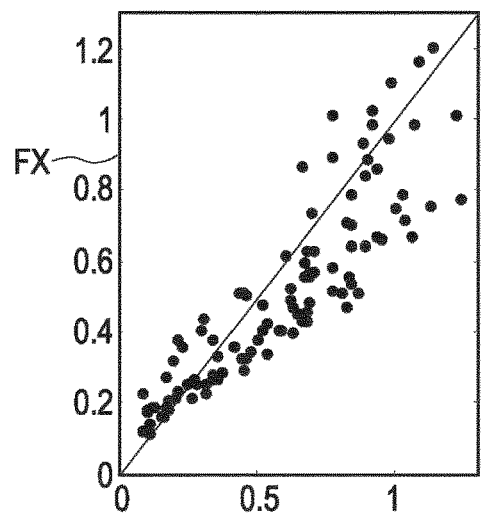
Figure 10E:
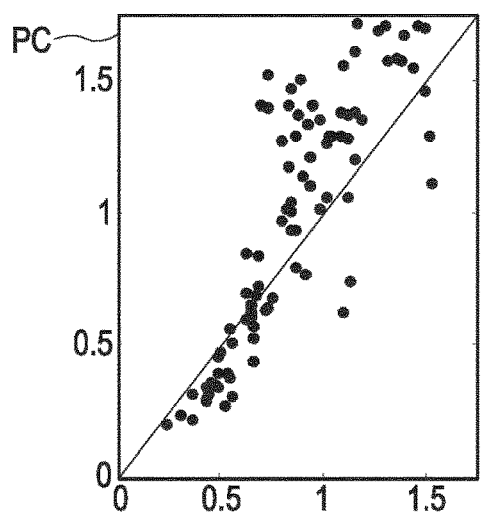

In contrast the level of agreement between the predicted concentrations values of vitamin K affected proteins FII, FVII, FIX, FX and PC using method A and the received concentration values derived from the blood samples is limited, as can be seen from the following table and FIG. 8A, and FIG. 9A. The slope of the linear regression based on these proteins, normalized by their population averages, is significantly lower than 1, namely 0.48, which indicates an underestimation of the predicted values, whereas the intercept is not zero indicating a systematic limitation of method A. The Lin's concordance correlation coefficient ($\rho_c$), which is a measure of agreement between two variables, is 0.55. Using the population distribution instead of the population estimates, as done in method B, does not significantly change the linear regression and $\rho_c$ (see FIG. 8B and FIG. 9B).

The results obtained using methods D and E for days 2 until 9 have an improved accuracy as is evident from the linear regression coefficients being closer to one for the slope and closer to zero for the intercept. Furthermore a higher $\rho_c$ can be derived for methods D and E, see days 2-9 and days 3-9 results shown in the following table.

The best samples derived in a first run of method E2 can be used as input for a subsequent run of method E2 in an iterative manner in order to repeat method E2 until a predetermined event occurs, e.g., a predetermined time passed or the time of surgery arrived. It is evident to the person skilled in the art that including a higher number of received values derived from measurements performed on the blood samples allows to increase the accuracy of the methods E2 and E (see FIG. 10A to 10E compared to FIG. 8D and FIG. 9D).

The following table comprises regression results of the four different methods A, B, D, and E using the PKPD model as depicted by slope (and its 95% confidence interval) of a linear regression and intercept of the linear regression (and its 95% confidence interval) and an agreement test of two variables, Lin's concordance correlation coefficient $\rho_c$:

|  |  | Method A | Method B | Method D | Method E |
|---|---|---|---|---|---|
| All days (n = 535) | $\rho_c$ | 0.55 | 0.58 | 0.67 | 0.77 |
|  | slope | 0.48 | 0.50 | 1.03 | 0.97 |
|  |  | (0.44-0.52) | (0.46-0.55) | (0.94-1.11) | (0.97-1.03) |
|  | intercept | 0.18 | 0.20 | 0.002 | −0.01 |
|  |  | (0.14-0.22) | (0.16-0.24) | (−0.08-0.08) | (−0.07-0.05) |
| Days 2-9 (n = 475) | $\rho_c$ | 0.39 | 0.42 | 0.65 | 0.75 |
|  | slope | 0.36 | 0.37 | 0.88 | 0.92 |
|  |  | (0.32-0.40) | (0.33-0.42) | (0.79-0.97) | (0.85-0.99) |
|  | intercept | 0.30 | 0.33 | 0.19 | 0.12 |

|  |  | Method A | Method B | Method D | Method E |
|---|---|---|---|---|---|
| Days 3-9 (n = 415) | $\rho_c$ | (0.25-0.35) 0.48 | (0.28-0.38) 0.51 | (0.10-0.29) 0.58 | (0.05-0.20) 0.72 |
|  | slope | 0.42 (0.37-0.47) | 0.43 (0.38-0.49) | 1.02 (0.90-1.13) | 0.98 (0.90-1.06) |
|  | intercept | 0.29 (0.24-0.33) | 0.30 (0.25-0.36) | −0.02 (−0.09-0.13) | −0.01 (−0.11-0.06) |

Figure 11A:
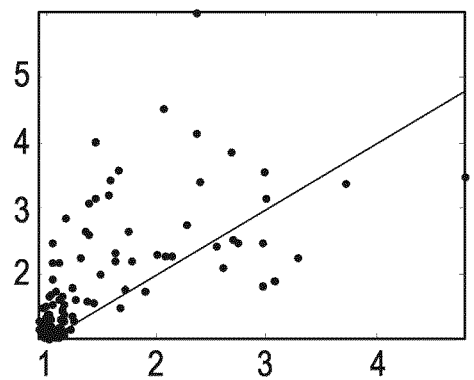
FIG. 11A to 11D show four correlation graphs of four different methods for predicted INR values compared to received INR values for the study setup of FIG. 7, FIG. 12A to 12E show five graphs of predicted concentration values to received concentration values of 5 coagulation factors for the study setup of FIG. 7 predicted by an embodiment of the method based on received INR values.
Figure 11B:
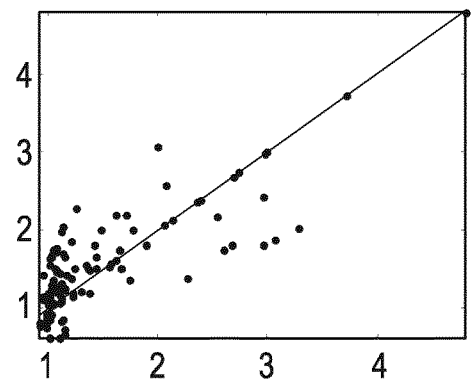

FIG. 11A shows a correlation graph of predicted INR values on the vertical axis compared to received INR values on the horizontal axis. The predicted INR values are predicted with method B based on system characteristics. FIG. 11B shows a correlation graph of predicted INR values on the vertical axis compared to received INR values on the horizontal axis. The predicted INR values are predicted with method D, i.e., based on INR values received at t1.

Figure 11C:
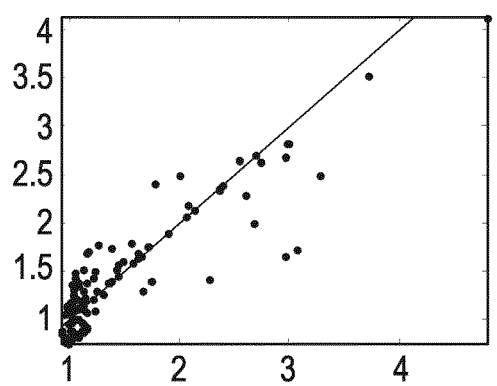

FIG. 11C shows a correlation graph of predicted INR values on the vertical axis compared to received INR values on the horizontal axis. The predicted INR values are predicted with method E based on INR values received at t1 and t2.

Figure 11D:
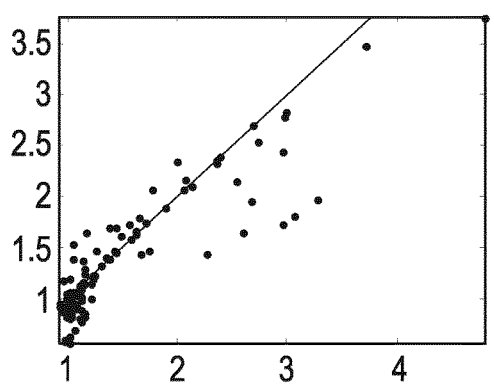
Figure 12A:
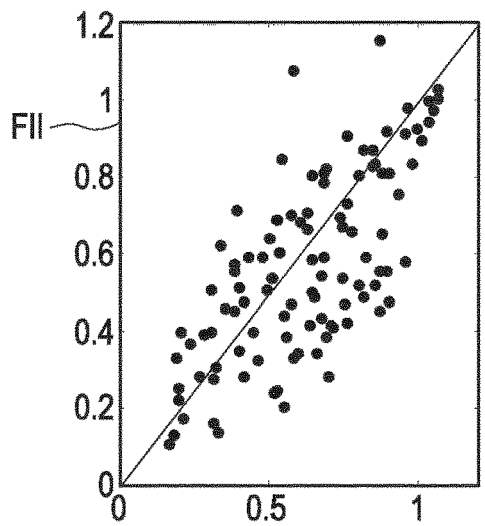
Figure 12B:
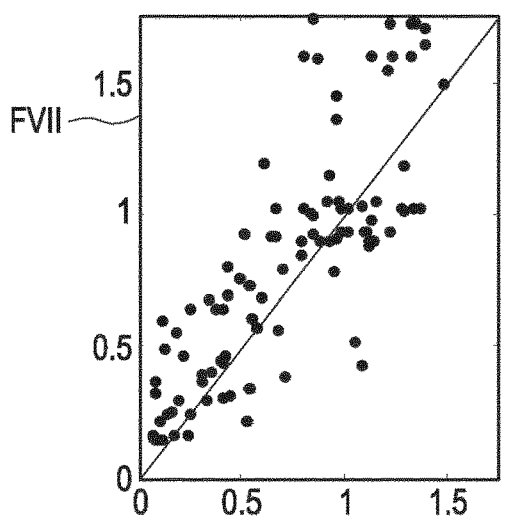
Figure 12C:
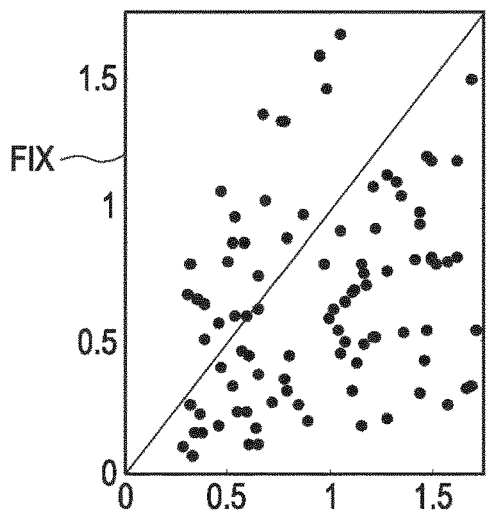
Figure 12D:
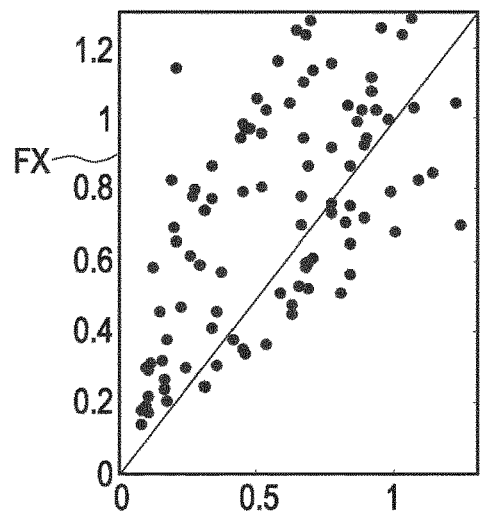
Figure 12E:
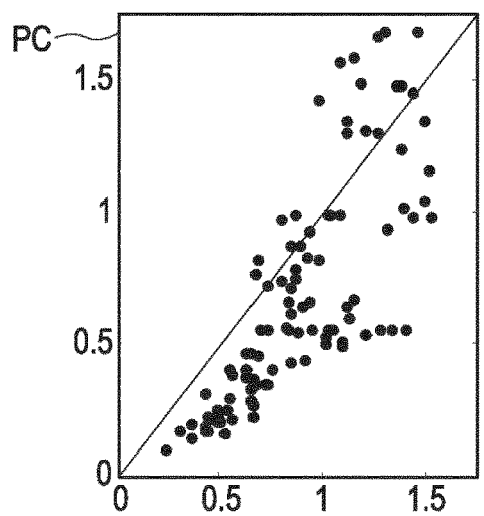

FIG. 11D shows a correlation graph of predicted INR values on the vertical axis compared to received INR values on the horizontal axis. The predicted INR values are predicted with method E based on INR values received at t1, t2, and t3.

It can be derived from FIG. 11A to FIG. 11D that the correlation between predicted INR values compared to received INR values improves by including more received INR values in the method for predicting the INR values.

FIG. 12A to FIG. 12E show correlation graphs of predicted concentration values of FII, FVII, FIX, FX, and PC on the vertical axis compared to received concentration values of FII, FVII, FIX, FX, and PC on the horizontal axis. The concentration values are normalized to the normal concentration values of the population average. The predicted concentration values are predicted with method E based on received INR values at the times t1, t2, and t3. The predicted concentration values show reasonable agreement compared to the received concentration values. Compared to the method used to predict the concentration values as presented in FIG. 10A to FIG. 10E only one value, i.e., the INR value needs to be derived from measurements at each time t1, t2, etc. This is cheaper than deriving five concentration values from measurements at each time t1, t2, etc.

While the invention has been illustrated and described in detail in the drawings and foregoing description, such illustration and description are to be considered illustrative or exemplary and not restrictive; the invention is not limited to the disclosed embodiments. For example, it is possible to operate the invention in an embodiment wherein more than one drug interaction is studied in order to predict a value of a parameter of the system.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit, processor, or device may fulfill the functions of several items recited in the claims. The mere fact that certain measures are recited in mutually different dependent claims does not indicate that a combination of these measures cannot be used to advantage.

Operations like receiving values of parameters of the system, predicting values of parameters of the system, incrementally optimizing a PKPD model based on values of the parameters of the system received over time, et cetera performed by one or several units or devices can be performed by any other number of units or devices. These operations and/or the control of the decision support system can be implemented as program code means of a computer program and/or as dedicated hardware.

A computer program may be stored/distributed on a suitable medium, such as an optical storage medium, or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a method for predicting a value of a parameter of a system. The value of the parameter of the system is predicted by incrementally optimizing a PKPD model based on values of parameters of the system received over time. This allows for predicting values of the parameters of the system with improved accuracy. In one embodiment the system comprises a coagulation system comprising an anticoagulant. The predicted value of the parameter of the system can be a point in time at which the coagulation system reaches hemostatic balance after a periodic supply of anticoagulant to the coagulation system is discontinued.

In further aspects, the present invention provides additional embodiments as defined in the following numbered paragraphs:

1. A method for predicting a value of a parameter of a system, wherein the value of the parameter of the system is predicted by incrementally optimizing a pharmacokinetic and pharmacodynamic model based on values of parameters of the system received over time.

2. The method according to paragraph 1, wherein the method comprises the steps receiving initial values of the parameters of the system,
   receiving a value or values of one or more of the parameters of the system, and
   predicting the value of the parameter of the system based on current values of the parameters of the system using the pharmacokinetic and pharmacodynamic model,
   wherein the steps of receiving a value or values of one or more of the parameters of the system and predicting the value of the parameter of the system are repeated until occurrence of a predetermined event.

3. The method according to paragraph 2, wherein the system comprises a coagulation system comprising an anticoagulant, and wherein the parameters of the system comprise parameters of the coagulation system.

4. The method according to paragraph 3, wherein the parameters of the system comprise a system characteristic of the system.
5. The method according to paragraph 4, wherein the received value or values of one or more of the parameters of the system comprise a value of a parameter of the coagulation system sensitive to the effects of the anticoagulant.
6. The method according to paragraph 2, wherein a sensitive parameter of the system is selected from the parameters of the system and wherein the sensitive parameter of the system is used to optimize the pharmacokinetic and pharmacodynamic model.
7. The method according to paragraph 6, wherein the sensitive parameter of the system is selected by a sensitivity analysis.
8. The method according to paragraph 6, wherein the step of predicting the value of the parameter of the system based on current values of the parameters of the system using the pharmacokinetic and pharmacodynamic model, comprises the step optimizing a current value of the sensitive parameter of the system by minimizing a difference between the received value or values of one or more of the parameters of the system and its predicted current value or their predicted current values based on variation of the current value of the sensitive parameter of the system while keeping values of other parameters of the system fixed.
9. The method according to paragraph 2 or 8, wherein one or more of the parameters have two or more initial values, and wherein the step of receiving initial values of the parameters of the system, comprises the step generating a number of random samples from the initial values of the parameters as input for the prediction of the value of the parameter of the system.
10. The method according to paragraph 3, wherein the predicted value of the parameter of the system is an international normalized ratio value, a time until the international normalized ratio value reaches a predetermined threshold value, a concentration value of a coagulation factor, or a time until one or more values of one or more coagulation factors reach predetermined threshold values.
11. The method according to paragraph 2 or 3, which further comprises the step:
performing an action based on the predicted value of the parameter of the system, wherein the step of performing an action based on the predicted value of the parameter of the system is performed whenever the value of the parameter of the system is predicted.
12. A decision support system (10) comprising:
a receiving unit (12) for receiving values of parameters of a system (20), and
a system unit (14) for predicting a value of a parameter of the system (20), wherein the receiving unit (14) is configured to supply received values of the parameters of the system (20) to the system unit (14), and wherein the system unit (14) is configured to predict the value of the parameter of the system (20) by incrementally optimizing a pharmacokinetic and pharmacodynamic model based on values of the parameters of the system (20) received over time.
13. The decision support system (10) according to paragraph 12 comprising:
a user interface (16), wherein the user interface (16) is configured to supply received values of the parameters of the system (20) to the system unit (14) and to receive predicted values of the parameters of the system (20) from the system unit (14), and wherein the user interface (16) is configured to receive by a user (22) using the decision support system (10) as input to the decision support system (10) a value of a parameter of the system (20) and to provide to the user (22) using the decision support system (10) as output of the decision support system (10) the value of the parameter predicted by the system unit (14).
14. A computer program for predicting a value of a parameter of a system (20), wherein the computer program comprises program code means for causing a processor to carry out the method as defined in paragraph 1, when the computer program is run on the processor.
15. Computer readable medium (24) comprising a computer program according to paragraph 14.

The invention claimed is:
1. A computer-implemented method for improving a delivery of an anticoagulant treatment to a coagulation system of a subject,
the computer-implemented method comprising the steps of:
operating a drug unit to periodically supply the anticoagulant treatment to the coagulation system of the subject;
during the periodic supplying of the anticoagulant treatment to the coagulation system of the subject by the drug unit, predicting a value of a parameter of the coagulation system including:
receiving initial values of the parameters of the coagulation system of the subject;
receiving a value or values of one or more of the parameters of the coagulation system of the subject subsequent to the receiving the initial values of the parameters of the coagulation system of the subject;
selecting one or more parameters of the coagulation system of the subject sensitive to the effects of the anticoagulant treatment;
predicting the value of the parameter of the coagulation system based on current values of the one or more selected parameters of the coagulation system of the subject using a combination pharmacokinetic and pharmacodynamic model, wherein the one or more selected parameters of the coagulation system are used to increment the combination pharmacokinetic and pharmacodynamic model,
wherein the steps of receiving the value or values of the one or more of the parameters of the coagulation system of the subject subsequent to the receiving the initial values of the parameters of the coagulation system of the subject and predicting the value of the parameter of the coagulation system of the subject are repeated until an occurrence of a predetermined event; and
upon the occurrence of the predetermined event, operating the drug unit to supply the anticoagulant treatment to the coagulation system of the subject based on the occurrence of the predetermined event.
2. The computer-implemented method according to claim 1, wherein the one or more selected parameters of the coagulation system of the subject are selected by an analysis the parameters of the coagulation system of the subject sensitive to the effects of the anticoagulant treatment.
3. The computer-implemented method according to claim 1, wherein the step of predicting the value of the parameter of the coagulation system of the subject based on current values of the parameters of the coagulation system using the combination pharmacokinetic and pharmacodynamic model, includes:

optimizing a current value of the one or more selected parameters of the coagulation system of the subject by minimizing a difference between the received value or values of one or more of the parameters of the coagulation system of the subject and its predicted current value or their predicted current values based on a variation of the current value of the one or more selected parameters of the coagulation system of the subject while keeping values of other parameters of the coagulation system of the subject fixed.

4. The computer-implemented method according to claim 1, wherein one or more of the parameters have two or more initial values, and wherein the step of receiving initial values of the parameters of the coagulation system of the subject, includes:

generating a number of random samples from the initial values of the parameters as input for the prediction of the value of the parameter of the coagulation system of the subject.

5. The computer-implemented method according to claim 1, wherein the predicted value of the parameter of the coagulation system of the subject is one of:

an international normalized ratio (INR) value;
    a time until the international normalized ratio value reaches a predetermined threshold value;
    a concentration value of a coagulation factor; or
    a time until one or more values of one or more coagulation factors reach predetermined threshold values.

6. The computer-implemented method according to claim 1, wherein the predicted value of the parameter of the coagulation system of the subject is a time interval or point in time at which the coagulation system of the subject interacting with the anticoagulant treatment reaches hemostatic balance after discontinuing a periodic supply of anticoagulant treatment to the coagulation system of the subject.

7. The computer-implemented method according to claim 6, wherein the hemostatic balance is indicated by an INR value between 0.8 and 1.2.

8. The computer-implemented method according to claim 1, wherein the predicted value of the parameter of the coagulation system of the subject is a time interval or point in time at which the coagulation system of the subject interacting with the anticoagulant treatment reaches a state in which a surgical procedure can be performed with an acceptable bleeding risk.

9. The computer-implemented method according to claim 8, wherein an acceptable bleeding risk is indicated by an INR value below 1.5.

10. The computer-implemented method according to claim 1, wherein the operating the drug unit to supply the anticoagulant treatment to the coagulation system of the subject based on the occurrence of the predetermined event includes:

indicating an action to be performed based on the predicted value of the parameter of the coagulation system of the subject, wherein the step of indicating an action to be performed based on the predicted value of the parameter of the coagulation system of subject is performed whenever the value of the parameter of the coagulation system subject is predicted.

11. The computer-implemented method according to claim 10, wherein the action includes continuing supply of the anticoagulant treatment to the coagulation system of the subject by the drug unit, discontinuing supply of the anticoagulant treatment to the coagulation system of the subject by the drug unit, or supplying vitamin K to the coagulation system of the drug unit.

12. A decision support system for improving a delivery of an anticoagulant treatment to a coagulation system of a subject, the decision support system comprising:

a drug unit for supplying the anticoagulant treatment to the coagulation system of the subject;
    a system unit for operating the drug unit to periodically supplying the anticoagulant treatment to the coagulation system of the subject;
    a receiving unit for receiving values of parameters of the coagulation system of the subject interacting with the anticoagulant treatment periodically supplied to the coagulation system of the subject by the drug unit;
    wherein the system unit is configured to predict a value of a parameter of the coagulation system of the subject as a basis for improving an interaction of the coagulation system of the subject with the anticoagulant treatment;
    wherein the receiving unit is configured to supply received values of the parameters of the coagulation system of the subject to the system unit;
    wherein the system unit is further configured to select one or more parameters of the coagulation system of the subject sensitive to the effects of the anticoagulant treatment and to predict the value of the parameter of the coagulation system of the subject by incrementing a combination pharmacokinetic and pharmacodynamic model based on values of the one or more selected parameters of the coagulation system of the system during the periodic delivery of the anticoagulant treatment to the coagulation system of the subject by the drug unit;
    wherein, during the periodic delivery of the anticoagulant treatment to the coagulation system of the subject by the drug unit, the receiving unit is further configured to repeat receiving the value or values of the one or more of the parameters of the coagulation system of the subject subsequent to the receiving the initial values of the parameters of the coagulation system of the subject and the system unit is further configured to repeat predicting the value of the parameter of the coagulation system until an occurrence of a predetermined event; and
    wherein, upon the occurrence of the predetermined event, the system unit is further configured to operate the drug unit to supply the anticoagulant treatment to the coagulation system of the subject based on the occurrence of the predetermined event.

13. The decision support system according to claim 12 further comprising:

a user interface,
        wherein the user interface is configured to supply received values of the parameters of the coagulation system of the subject to the system unit and to receive predicted values of the parameters of the coagulation system of the subject from the system unit, and
        wherein the user interface is configured to receive by a user using the decision support system as input to the decision support system a value of a parameter of the coagulation system of the subject and to provide to the user using the decision support system as output of the decision support system the value of the parameter of the coagulation system of the subject predicted by the system unit.

14. A non-transitory computer readable medium comprising a computer program which, when executed on a computing device, carries out a method for improving a delivery of an anticoagulant treatment to a coagulation system of a subject, wherein the computer program comprises program code to:
   operate a drug unit to periodically supply the anticoagulant treatment to the coagulation system of the subject;
   during the periodic supplying of the anticoagulant treatment to the coagulation system of the subject by the drug unit, predict a value of a parameter of the coagulation system including
      receive initial values of the parameters of the coagulation system of the subject;
      receive a value or values of one or more of the parameters of the coagulation system of the subject subsequent to the receiving the initial values of the parameters of the coagulation system of the subject;
      select one or more parameters of the coagulation system of the subject sensitive to the effects of the anticoagulant treatment; and
      predict the value of the parameter of the coagulation system of the subject based on current values of the one or more selected parameters of the coagulation system of the subject using a combination of pharmacokinetic and pharmacodynamic model, wherein the one or more selected parameters of the system are used to increment the combination pharmacokinetic and pharmacodynamic model,
   wherein receiving the value or values of the one or more of the parameters of the coagulation system of the subject subsequent to the receiving the initial values of the parameters of the coagulation system of the subject and predicting the value of the parameter of the coagulation system of the subject are repeated until occurrence of a predetermined event; and
   upon the occurrence of the predetermined event, operate the drug unit to supply the anticoagulant treatment to the coagulation system of the subject based on the occurrence of the predetermined event.

* * * * *